(12) United States Patent
Xu et al.

(10) Patent No.: US 9,551,656 B2
(45) Date of Patent: Jan. 24, 2017

(54) ABSORPTION AND SCATTERING EFFECTS SEPARATION FROM DIFFUSE SPECTRUM DATA AND MODEL ESTABLISHMENT AND CONCENTRATION PREDICTION BASED THEREON

(71) Applicant: Tianjin Sunrise Technologies Development Co., Ltd., Tianjin (CN)

(72) Inventors: Kexin Xu, Tianjin (CN); Jin Liu, Tianjin (CN)

(73) Assignee: TIANJIN SUNRISE TECHNOLOGIES DEVELOPMENT CO., LTD., Tianjin (CN)

( * ) Notice: Subject to any disclaimer, the term of this patent is extended or adjusted under 35 U.S.C. 154(b) by 0 days.

(21) Appl. No.: 14/705,006

(22) Filed: May 6, 2015

(65) Prior Publication Data
US 2015/0346090 A1    Dec. 3, 2015

(30) Foreign Application Priority Data
May 28, 2014    (CN) .......................... 2014 1 0233900

(51) Int. Cl.
| | |
|---|---|
| G01N 21/49 | (2006.01) |
| G01N 21/27 | (2006.01) |
| G01N 21/47 | (2006.01) |
| A61B 5/145 | (2006.01) |
| A61B 5/1455 | (2006.01) |

(52) U.S. Cl.
CPC .............. *G01N 21/49* (2013.01); *G01N 21/27* (2013.01); *G01N 21/274* (2013.01); *G01N 21/47* (2013.01); *G01N 21/4738* (2013.01); *A61B 5/1455* (2013.01); *A61B 5/14532* (2013.01)

(58) Field of Classification Search
CPC ... A61B 5/14532; A61B 5/1455; G01N 21/27; G01N 21/49; G01N 21/47; G01N 21/4795; G01N 21/59; G01N 33/66; G02B 6/04
USPC ....... 356/317, 303, 614, 319, 326, 432–440; 702/19; 600/476
See application file for complete search history.

(56) References Cited

U.S. PATENT DOCUMENTS

| | | | |
|---|---|---|---|
| 2003/0023152 A1* | 1/2003 | Abbink ............... | A61B 5/0075 600/316 |
| 2006/0167348 A1* | 7/2006 | Arnold ............... | A61B 5/14532 600/310 |
| 2006/0247532 A1* | 11/2006 | Ramanujam ......... | A61B 5/0091 600/476 |
| 2012/0140891 A1* | 6/2012 | Tabary ................ | G01N 23/046 378/84 |
| 2016/0011103 A1* | 1/2016 | Morishima ......... | G01N 21/3577 435/165 |
| 2016/0091496 A1* | 3/2016 | Xu ....................... | G02B 6/3624 356/436 |
| 2016/0249836 A1* | 9/2016 | Gulati ................. | A61B 5/1455 |

\* cited by examiner

*Primary Examiner* — Hoa Pham
(74) *Attorney, Agent, or Firm* — Westman, Champlin & Koehler, P.A.

(57) ABSTRACT

A method of processing diffuse spectrum data may include: obtaining diffuse spectrum data of a medium to be detected at one or more first radial positions; and determining optical information caused by substantially only a variation in scattering characteristic of the medium to be detected and/or optical information caused by substantially only a variation in absorption characteristic of the medium to be detected at one or more second radial positions from the obtained diffuse spectrum data.

30 Claims, 14 Drawing Sheets

ABSORPTION AND SCATTERING EFFECTS SEPARATION FROM DIFFUSE SPECTRUM DATA AND MODEL ESTABLISHMENT AND CONCENTRATION PREDICTION BASED THEREON

CROSS-REFERENCE TO RELATED APPLICATION(S)

This application claims priority to Chinese Application No. 201410233900.0, filed on May 28, 2014, which is incorporated herein by reference in its entirety.

TECHNICAL FIELD

The present disclosure generally relates to the field of spectroscopy, and more particularly, to absorption and scattering effects separation from diffuse spectrum data and model establishment and concentration prediction based thereon.

BACKGROUND

The spectroscopy technology has various advantages, such as environmental benefits, pollution-free, no damages to samples, fast detection speed, simultaneous quantitative analyses of multiple components, no need for any reagents or test paper, continuous and real-time monitoring, or the like. It is a real nondestructive detection technique.

In actual applications, substances to be detected are generally complex samples without being subjected to pre-processing such as refinement, that is, scattering media, such as milk, organic tissues, or the like. These scattering media are characterized by exhibiting strong scattering and also strong absorption in the near-infrared band. As compared with pure-absorptive media, spectra detected from the scattering media include both effects of scattering and absorption. In this case, the Beer-lambert Law is no longer applicable. Further, due to strong scattering effects of particles in the scattering media, most light is diffused light. Diffused photons have travelling paths, which are not fixed but vary with optical parameters of the media such as absorption and scattering characteristics. Therefore, detection of component(s) in the scattering medium by the spectroscopy is susceptible to interferences from changes in the optical parameters of the medium itself, especially, from changes in the scattering characteristic, and thus so far it cannot achieve the detection accuracy as already achieved in the detection in the pure-absorptive media.

At present, the component detection in the scattering media has succeeded in scenarios where the component has a relatively great concentration and exhibits relatively strong absorption. In such scenarios, the absorption effect is considered as being predominant, while omitting optical path changes caused by the scattering effect, which are relatively small. Examples of such scenarios include detection of degree of blood oxygen saturation and detection of hemoglobin based on photoelectric pulse wave. The hemoglobin is the main absorptive component of the blood, has a relatively great concentration, and exhibits relatively strong absorption in the near-infrared band. Therefore, the Beer-Lambert Law is considered as being approximately applicable in scenarios of thin-layer-media. However, the detection accuracy of the hemoglobin is not very high. For components with a relatively small content and relatively small absorption, such as blood sugar and albumin, the detection accuracy is low, and thus cannot satisfy precision requirements in actual applications. Therefore, detection of weak components in the scattering media becomes an obstacle in the spectroscopy.

In addition, the spectroscopy needs a model established for a particular scattering media, and it is difficult to transfer models between each other. For example, a detection mode established for a batch of milk will generally cause significant errors if used for another batch of milk. Furthermore, it is difficult for different types of scattering media to share models. For example, a model for milk is not suitable for component detection of organic tissues.

Mainly due to the two defects, that is, low detection accuracy and non-portability of models, the spectroscopy is limited in the applications of component detection in the scattering media. However, there is a potential need for the spectroscopy in applications such as food safety detection, environmental safety detection, and non-invasive detection of organic tissues due to its advantages such as properties of being non-destructive, real-time, and online.

SUMMARY

The present disclosure aims to provide, among others, a method of processing diffuse spectrum data, by which it is possible to effectively separate optical information caused by substantially only a scattering effect and optical information caused by substantially only an absorption effect, and also methods of establishing a prediction model and of concentration prediction based on the separated information, and also a processing apparatus.

According to an aspect of the present disclosure, there is provided a method of processing diffuse spectrum data. The method may comprise: obtaining diffuse spectrum data of a medium to be detected at one or more first radial positions; and determining optical information caused by substantially only a variation in scattering characteristic of the medium to be detected and/or optical information caused by substantially only a variation in absorption characteristic of the medium to be detected at one or more second radial positions from the obtained diffuse spectrum data.

According to a further aspect of the present disclosure, there is provided a method of establishing a prediction model. The method may comprise: performing the above method on a series of media, wherein each of the series of media comprises a background or reference medium with a particular component at a respective known concentration added into the background or reference medium, wherein the reference medium comprises the background medium and the particular component at an initial concentration; and establishing the prediction model based on the respective known concentrations and the respective optical information caused by substantially only variations in scattering characteristics of the respective media and/or optical information caused by substantially only variations in absorption characteristics of the respective media.

According to a still further aspect of the present disclosure, there is provided a method of predicting a concentration. The method may comprise: performing the above method on a medium to be detected, which comprises a background or reference medium with a particular component at a concentration included in the background or reference medium, which concentration is unknown due to concentration change, wherein the reference medium comprises the background medium and the particular component at an initial concentration; and predicting the concentration of the particular component according to the prediction model established as described above based on at least one of the optical information caused by substantially only the variation in the scattering characteristic of the medium to be detected and the optical information caused by substantially only the variation in the absorption characteristic of the medium to be detected.

According to a still further aspect of the present disclosure, there is provided a method of predicting a concentration. The method may comprise: obtaining respective absorption coefficients or absorbance of a series of media, each of which comprises a pure-absorptive background medium with a particular component at a respective known concentration added into the pure-absorptive background medium; establishing a prediction model based on the respective known concentrations and the respective absorption coefficients or absorbance; obtaining diffuse spectrum data of a medium to be detected at a point insensitive to scattering, wherein the medium to be detected comprises a scattering background medium and the particular component at an unknown concentration due to change in concentration from an initial concentration; and predicting the concentration of the particular component according to the prediction model based on the diffuse spectrum data of the medium to be detected at the point insensitive to scattering, wherein the point insensitive to scattering indicates a radial position where light intensity information included in the spectrum data is substantially insensitive to a variation in scattering characteristic of the medium to be detected.

According to a still further aspect of the present disclosure, there is provided a processing apparatus. The apparatus may comprise: an detector configured to detect a spectrum of a medium to be detected; and a processor configured to determine optical information caused by substantially only variations in scattering characteristics of the medium to be detected and/or optical information caused by substantially only variations in absorption characteristics of the medium to be detected at one or more radial positions from the detection of the detector.

According to embodiments of the present disclosure, it is possible to extract the optical information caused by substantially only the variation in the scattering characteristic and/or the optical information caused by substantially only the variation in the absorption characteristic. Based on such information, it is possible to achieve a relatively high prediction accuracy. Especially, it is possible to extract substantially pure absorption information, which can be effectively used for concentration prediction.

BRIEF DESCRIPTION OF THE DRAWINGS

The above and other objects, features, and advantages of the present disclosure will become more apparent from following descriptions on embodiments thereof with reference to attached drawings, in which.

DETAILED DESCRIPTION

Hereinafter, descriptions are given with reference to embodiments shown in the attached drawings. However, it is to be understood that these descriptions are illustrative and not intended to limit the present disclosure. Further, in the following, known structures and technologies are not described to avoid obscuring the present disclosure unnecessarily.

The inventors have found that it is possible to separate an optical signal caused by a variation in scattering characteristic (generally expressed as a scattering coefficient $\mu_s$ or a reduced scattering coefficient $\mu_s'$) of various constituent particles in a scattering medium and an optical signal caused by a variation in absorption characteristic (generally expressed as an absorption coefficient $\mu_a$) thereof from superimposed diffuse spectrum data of the scattering medium. Here, the so-called "scattering medium" refers to a medium where there is a component exhibiting relatively strong scattering to light (and generally exhibiting also absorption) (which is different from a pure-absorptive medium, and thus the Beer-Lambert Law is no longer applicable). For example, the intralipid solution is a kind of fat milk, which is a suspension solution and exhibits strong scattering to light. Generally, the intralipid solution may be used to mimic optical characteristics of human skin, and may have glucose added therein to mimic detection of glucose in the skin.

Especially, at some particular detection positions, an "optical signal caused by (substantially) only a variation in scattering characteristic" (referred to as "pure scattering signal" in brief) and an "optical signal caused by (substantially) only a variation in absorption characteristic" (referred to as "pure absorption signal" in brief) can be obtained. Those two types of "pure signals" may embody effects of the scattering and absorption, respectively.

This is because of the observation of the inventors that a relative variation in light intensity exhibits monotonically increasing or decreasing linearity or approximate linearity as the detection distance goes further.

In the following, this rule will be explained by a stable solution of a diffusion equation in an infinite medium based on the theory of measurements in scattering media.

Figure 1:
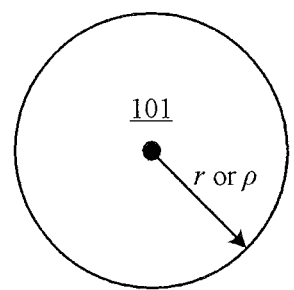
FIG. 1 is a schematic view showing spectrum detection.

As shown in FIG. 1, when detection is performed at a ring or spherical region at a distance of r from a light source 101, a detection distance $\rho=r$. In this case, a first-order approximate solution of light energy flux density $\Phi$ can be expressed as Equation (1).

$$\Phi(\rho) = \frac{1}{4\pi D\rho}\exp(-\mu_{\it{eff}} \cdot \rho) \tag{1}$$

where $\rho$ denotes a radial distance between a detector and the light source; $\mu_a$ denotes an absorption coefficient; $\mu_s'$ denotes a reduced scattering coefficient and is defined as $(1-g)\mu_s$, where g denotes an anisotropy factor, and $\mu_s$ denotes a scattering coefficient; D denotes a diffusion coefficient of photons, and is defined as $D=\{3[\mu_a+(1-g)\mu_s]\}^{-1}=[3(\mu_a+\mu_s')]^{-1}$; $\mu_{\it{eff}}$ denotes an effective attenuation coefficient, and is defined as $\mu_{\it{eff}}=\sqrt{3\mu_a\cdot[\mu_a+(1-g)\mu_s]}=\sqrt{3\mu_a\cdot(\mu_a+\mu_s')}$.

Assume that the scattering medium has an absorption coefficient of $\mu_a$, a scattering coefficient of $\mu_s$, an anisotropy factor of g, and a refractive index of n in an initial state, resulting in an initial spectrum, as shown by Equation (1). Further, assume that optical characteristics (such as, absorption and/or scattering characteristics) of the scattering medium are changed due to a concentration change of a component thereof (or even a change from 0 to some certain concentration, that is, addition of the component) or the like. Such a change may result in a change $\Delta\mu_a$ of the absorption coefficient and a change $\Delta\mu_s$ of the scattering coefficient, for example. In this case, the resultant light energy flux density may be changed by $d\Phi$ or $\Delta\Phi$. Total differential of Equation (1) results in Equation (2).

$$\begin{aligned}d\Phi &= \frac{\partial \Phi}{\partial \mu_a}d\mu_a + \frac{\partial \Phi}{\partial \mu_s'}d\mu_s' \\ &= \Phi\Big(3D - \frac{3}{2}\rho D\mu_{\it{eff}}\Big)\cdot d\mu_s' + \\ &\quad \Phi\Big(3D - \frac{1}{2}\rho(D^{-1}\mu_{\it{eff}}^{-1}+3D\mu_{\it{eff}})\Big)\cdot d\mu_a\end{aligned} \tag{2}$$

The light energy flux density $\phi$ represents light radiation intensity in a unit volume at a distance of $\rho$ from the light source, and the magnitude and variation thereof can reflect magnitude and variation of actually detected light intensity. Here, a relative variation S of the energy flux density is defined as $S=d\Phi/\Phi$. Then, S can be expressed as Equation (3) as derived from Equation (2).

$$\begin{aligned}S &= \frac{d\Phi}{\Phi} \\ &= \Big(3D - \frac{3}{2}\rho D\mu_{\it{eff}}\Big)\cdot d\mu_s' + \Big(3D - \frac{1}{2}\rho(D^{-1}\mu_{\it{eff}}^{-1}+3D\mu_{\it{eff}})\Big)\cdot d\mu_a\end{aligned} \tag{3}$$

As can be seen from Equation (3), as the absorption coefficient and/or the scattering coefficient of the scattering medium are changed, the relative variation S of the light energy flux density exhibits linearity along the detection distance $\rho$. Further, it can be observed that S can be separated into a variation caused by substantially only the change of the scattering characteristic($d\mu_s'$) (i.e., the first item of Equation (3)) and a variation caused by substantially only the change of the absorption characteristic ($d\mu_a$) (i.e., the second item of Equation (3)), and that those two variations also exhibit linearity, respectively. In practice, generally it is the light intensity that is detected. The light intensity is in a linear relationship with the light energy flux density when detection parameters such as reception area, angle and duration are fixed. Therefore, it can be inferred that a relative variation in light intensity also satisfies the above rule. In the following, the relative variation in light intensity is also denoted by S.

Figure 25:
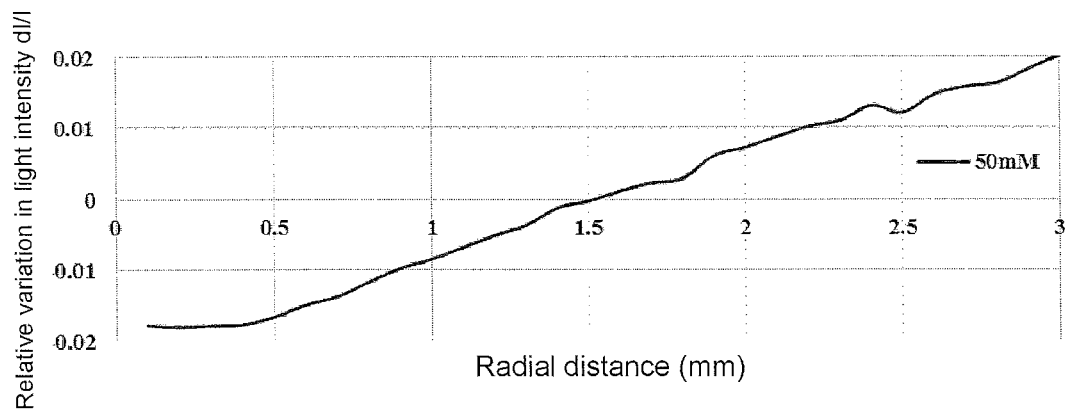
FIG. 25 is a graph showing substantial linearity of a relative variation in light intensity along a radial position axis resulting from simulation according to an embodiment of the present disclosure.

Though Equation (3) is derived in the case of infinite medium, the inventors have found that such a linearity rule is also applicable to half-infinite media. Some scattering media exhibit substantial linearity, though not exactly perfect linearity, in half-infinite detection scenarios, especially if the variation in light intensity is observed in a relatively small range of radial distances, not in an entire range of radial distances (i.e., from 0 to infinite). Therefore, it is feasible to adopt the linearity rule to approximate the half-infinite detection scenarios. The half-infinite detection scenarios often occur in practice, and the inventors have proved by experiments and simulations that the linearity rule is also applicable to those scenarios. For example, the inventors conducted a half-infinite detection experiment of a solution which is a scattering medium, where the light source is positioned above the medium, and the medium extends downward with a great thickness (approximate to infinite). In this case, light intensities at different distances from the light source were detected. It is found that the relative variation S of the light intensity exhibits substantial linearity along the radial distance, as shown by the solid line in FIG. 16. Further, the inventors simulated the half-infinite detection by simulating a situation where $10^8$ photons randomly travel in a scattering medium by means of Monte Carlo simulation. Specifically, a relative change in light intensity in a 3% intralipid solution, which is a scattering medium, with a change of 50 mM in concentration of glucose is simulated. The number of photons exited at various radial positions can reflect the intensity of the exited light, and a relative change in the number of the exited photons can reflect a relative variation S in the existed light intensity. FIG. 25 illustrates a relationship between S and the radial distance $\rho$. It can be seen that the linearity is strongly presented apart from the light source by more than a relatively small distance, for example, 0.5 mm.

On the other hand, a variation in light intensity can be expressed as:

$$\Delta I_i(\rho) = \Delta I_{C_i}(\rho) - \Delta I_{C_o}(\rho) = \frac{\partial I(\rho)}{\partial \mu'_s} \Delta \mu'_s + \frac{\partial I(\rho)}{\partial \mu_a} \Delta \mu_a \quad (4)$$

where $\rho$ denotes a radial distance, $I_{C_i}(\rho)$ denotes a light intensity detected when a particular component in a scattering medium has a concentration of $C_i$, $I_{C_o}(\rho)$ denotes a light intensity detected when the scattering medium has no such a particular component or the particular component has a certain initial concentration, $\mu'_s$ denotes a reduced scattering coefficient of the scattering medium, $\mu_a$ denotes an absorption coefficient of the scattering medium, $\partial I(\rho)/\partial \mu'_s$ denotes a rate of variation in light intensity $I(\rho)$ at the radial distance $\rho$ relative to the reduced scattering coefficient $\mu'_s$, $\partial I(\rho)/\partial \mu_a$ denotes a rate of variation in light intensity $I(\rho)$ at the radial distance $\rho$ relative to the absorption coefficient $\mu_a$, $\Delta \mu'_s$ denotes a variation of the reduced scattering coefficient, and $\Delta \mu_a$ denotes a variation of the absorption coefficient.

Here, the variations of the scattering coefficient (or the reduced scattering coefficient) and the absorption coefficient are caused by a combination of various factors, as shown in Equation (5). In the Equation, j denotes a factor which impacts the optical parameters of the medium, such as the concentration of a component (even a variation from 0 to a certain value, i.e., addition of this component). A variation of the factor j can affect both the absorption coefficient and the scattering coefficient (or the reduced scattering coefficient).

$$\Delta I(\rho) = \frac{\partial I(\rho)}{\partial \mu'_s} \cdot \sum_j \Delta \mu'_{s,j}(\lambda) + \frac{\partial I(\rho)}{\partial \mu_a} \cdot \sum_j \Delta \mu_{a,j}(\lambda) \quad (5)$$

where $\Delta \mu_{s,j}'(\lambda)$ denotes a variation in the reduced scattering coefficient caused by the factor j, and $\Delta \mu_{a,j}(\lambda)$ denotes a variation in the absorption coefficient caused by the factor j.

Figure 2:
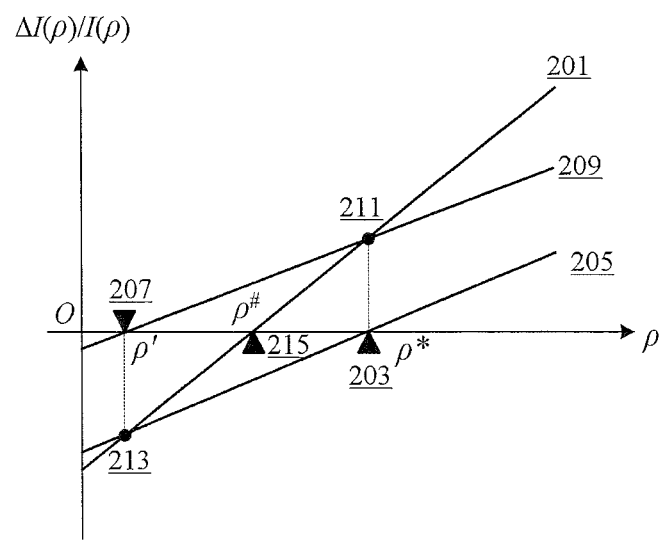
FIG. 2 is a schematic view showing separation of spectrum data according to an embodiment of the present disclosure.

For convenience of separation, we use the relative variation in light intensity for processing. That is, the expression of S is used in analyzing multi-factor variation cases. Specifically, Equation (3) expressing S in the infinite medium scenario is substituted in Equation (5), and then Equation (5) becomes Equation (6). As described above, the relative variation S in light intensity exhibits (substantial) linearity along the radial detection distance, as shown in FIG. 2. With respect to any single factor j among multiple factors, it also exhibits (substantial) linearity along the distance $\rho$. Here, such linearity is called an "effect line" for the factor j. A result from effects of the multiple factors can be represented by addition of multiple effect lines for the respective factors, which is also a linear "effect line."

$$S = \frac{\Delta I(\rho)}{I(\rho)} \quad (6)$$

$$= \frac{1}{I(\rho)} \cdot \left( \frac{\partial I(\rho)}{\partial \mu'_s} \cdot \sum_j \Delta \mu'_{s,j}(\lambda) + \frac{1}{I(\rho)} \cdot \frac{\partial I(\rho)}{\partial \mu_a} \cdot \sum_j \Delta \mu_{a,j}(\lambda) \right)$$

$$= \left( 3D - \frac{3}{2} \rho D \mu_{eff} \right) \cdot \sum_j \Delta \mu'_{s,j}(\lambda) +$$

$$\left( 3D - \frac{1}{2} \rho (D^{-1} \mu_{eff}^{-1} + 3D \mu_{eff}) \right) \cdot$$

$$\sum_j \Delta \mu_{a,j}(\lambda))$$

where $\lambda$ denotes the wavelength of the probe light. This is because that the scattering coefficient (or the reduced scattering coefficient) and the absorption coefficient may vary with the wavelength of the probe light.

It is to be noted that in this application the calculation of the relative variation in light intensity may be replaced by a calculation of a (natural) logarithm operation followed by a subtraction operation, for convenience of calculations (by, for example, converting the division operation into the subtraction operation). However, such a calculation is not necessary for the technology disclosed herein.

As shown in FIG. 2, the relative variation in light intensity $(\Delta I(\rho)/I(\rho))$ exhibits (substantial) linearity along the radial position axis $(\rho)$, as described above. In FIG. 2, a straight line 201 shows such a linear variation, and is called as a "composite effect line" (representing optical information caused by both the scattering and absorption effects), which contains scattering variation information and absorption variation information caused by variations of the respective components or factors in the scattering medium.

Further, a straight line 205 in FIG. 2 shows the first item in Equation (3) (relevant to $d\mu_s'$) or the first item in Equation (6) (relevant to $\Delta \mu_{s,j}'(\lambda)$), that is, optical information (for example, variation in light intensity) caused by substantially only the variation in the scattering characteristic, and thus may be called as a "scattering effect line" here. A straight line 209 in FIG. 2 shows the second item in Equation (3) (relevant to $d\mu_a$) or the second item in Equation (6) (relevant to $\Delta \mu_{a,j}(\lambda)$), that is, optical information (for example, variation in light intensity) caused by substantially only the variation in the absorption characteristic, and thus may be called as an "absorption effect line" here. As described above, those two items also exhibit linearity, respectively.

In other words, the scattering effect line can indicate representations of the "optical information (or signal) caused by substantially only the variation in the scattering characteristic" at various radial detection positions, and the absorption effect line can indicate representations of the "optical information (or signal) caused by substantially only the variation in the absorption characteristic" at various radial detection positions. On the other hand, the composite effect line mainly reflects optical information or signal caused by direct or indirect variations in the absorption coefficient and the scattering coefficient (or the reduced scattering coefficient) in combination. The composite effect line may be an actual detection result of the light intensity variation. The composite result can be separated into the scattering effect line and the absorption effect line, which can be used for analyses of absorption information and scattering information, respectively.

Here, concepts of a point 203 insensitive to scattering, a point 207 insensitive to absorption, and a composite floating reference point 215, which are zero-crossing points of the scattering effect line 205, the absorption effect line 209, and the composite effect line 201, respectively, may be also introduced.

Here, the word "floating" means that the point might be different under different conditions, for example, for different media, at different wavelengths, under different temperatures, or the like. For a particular medium (with, for example, a possible change in concentration of a particular component in the medium), the point insensitive to scattering, the point insensitive to absorption, and the composite reference point may be relatively steady, and the word "insensitive" may specifically refer to that the light intensity at the point insensitive to scattering do not change substantially due to variation in scattering caused by the change in concentration of the particular component, that the light intensity at the point insensitive to absorption do not change substantially due to variation in absorption caused by the change in concentration of the particular component, and that the light intensity at the composite reference point do not change substantially due to the change in concentration of the particular component.

If $$\frac{\partial I(\rho)}{\partial \mu_s} = 0$$

holds true at a position under a certain wavelength, then "optical information caused by (substantially) only variation in absorption" can be achieved at this position. Such a position is defined as the point 203 insensitive to scattering, and is labeled as $\rho^*$. According to Equation (3) (let the first item be zero), it can be derived:

$$\rho^* = \frac{2}{\mu_{eff}} \quad (7)$$

If $$\frac{\partial I(\rho)}{\partial \mu_a} = 0$$

holds true at a position under a certain wavelength, then "optical information caused by (substantially) only variation in scattering" can be achieved at this position. Such a position is defined as the point 207 insensitive to absorption, and is labeled as $\rho'$. According to Equation (3) (let the second item be zero), it can be derived:

$$\rho' = \frac{6}{D^{-2}\mu_{eff}^{-1} + 3\mu_{eff}} \quad (8)$$

If $$\Delta I(\rho) = \frac{\partial I(\rho)}{\partial \mu_s'}\Delta\mu_s' + \frac{\partial I(\rho)}{\partial \mu_a}\Delta\mu_a = 0$$

holds true at a position under a certain wavelength due to both the scattering and absorption effects, then it is the zero-crossing point of the composite effect line. This position is defined as the composite floating reference point 215, and is labeled as $\rho^\#$. According to Equation (3) (let the sum of the two items be zero), it can be derived:

$$\rho^\# = \frac{6*d\mu_s' + 6 \cdot d\mu_a}{3\mu_{eff} + d\mu_s' + (D^{-2}\mu_{eff}^{-1} + 3\mu_{eff}) \cdot d\mu_a} \quad (9)$$

Figure 3:
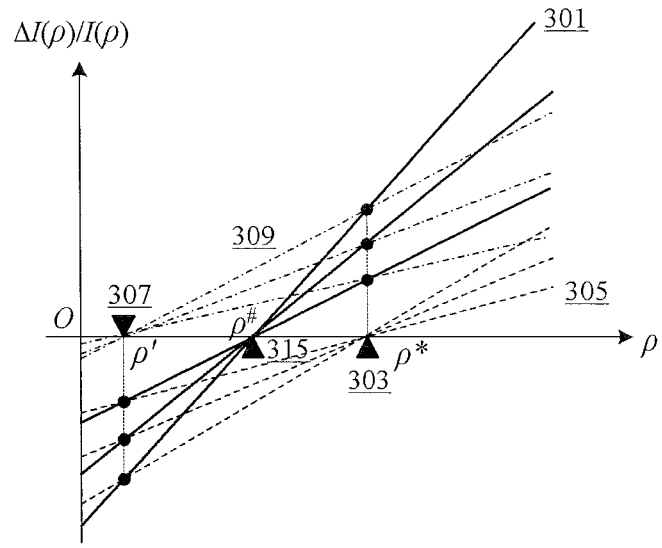
FIG. 3 is a schematic view showing separation of spectrum data at different concentrations of a particular component according to an embodiment of the present disclosure.

Further, effects of the various components are considered. As shown in Equation (6), for a particular component, assume that a variation in absorption coefficient and a variation in scattering coefficient caused thereby are directly proportional to its concentration. When the concentration varies in a relatively small range, differential forms of the respective factors (as shown in Equation (10)) can be substituted in Equation (6), resulting in Equation (11). Also, there is a fixed composite reference point for this component, which can be derived by solving Equation (12). In this case, the separation of the scattering effect line and the absorption effect line is shown in FIG. 3.

$$\Delta\mu_{s,j}'(\lambda) = \sum_j \frac{\partial \mu_s'}{\partial C_j} \cdot \Delta C_j, \Delta\mu_{a,j}(\lambda) = \sum_j \frac{\partial \mu_a}{\partial C_j} \cdot \Delta C_j \quad (10)$$

$$\frac{\Delta I(\rho)}{I(\rho)} = \sum_j \left(\frac{1}{I(\rho)} \cdot \frac{\partial I(\rho)}{\partial \mu_s} \cdot \frac{\partial \mu_s'}{\partial C_j} + \frac{1}{I(\rho)} \cdot \frac{\partial I(\rho)}{\partial \mu_a} \cdot \frac{\partial \mu_a}{\partial C_j}\right) \cdot \Delta C_j \quad (11)$$

$$\frac{1}{I(\rho)}\left(\frac{\partial I(\rho)}{\partial \mu_s} \cdot \frac{\partial \mu_s'}{\partial C_j} + \frac{\partial I(\rho)}{\partial \mu_a} \cdot \frac{\partial \mu_a}{\partial C_j}\right) = 0 \quad (12)$$

where $\partial\mu_s'/\partial C_j$ denotes a rate of variation in the reduced scattering coefficient $\mu_s'$ relative to a concentration $C_j$ of component j, $\partial\mu_a/\partial C_j$ denotes a rate of variation in the absorption coefficient $\mu_a$ relative to the concentration $C_j$ of component j, and $\Delta C_j$ denotes a variation in the concentration $C_j$ of component j.

Referring to FIG. 3, when a particular component has it concentration varied in the same scattering medium (three different concentration variations are shown in FIG. 3), respective composite effect lines 301, scattering effect lines 305, and absorption effect lines 309 are obtained, with respective composite reference points 315, points 303 insensitive to scattering, and points 307 insensitive to absorption at substantially fixed positions, respectively. The inventors have found that this rule applies even if the optical parameters (especially, the scattering coefficient) of the scattering medium vary in a great range (for example, a variation in scattering coefficient less than 50%). The main factor affecting the spectrum detection is fluctuations of the scattering coefficient, while the absorption variation can be deemed as a signal. In practice, such a great range of fluctuations of the scattering coefficient rarely occurs. This implies that this rule applies to general spectrum detections. On the other hand, for the particular component, the variation of its concentration can be limited to a certain range, because detection of the particular component (at a high accuracy) in the scattering medium is discussed here. For a scenario where the detection range is relatively wide (that is, a scenario where the concentration of the particular component varies greatly), such a great variation in concentration may cause the medium itself changed, and thus the medium can be deemed as different media in different detection ranges. Indeed, for a relatively small detection range, the rule that the composite reference point, the point insensitive to scattering, and the point insensitive to absorption are substantially fixed still applies. In other words, this rule generally holds true for concentration detections by spectroscopy.

Figure 4:
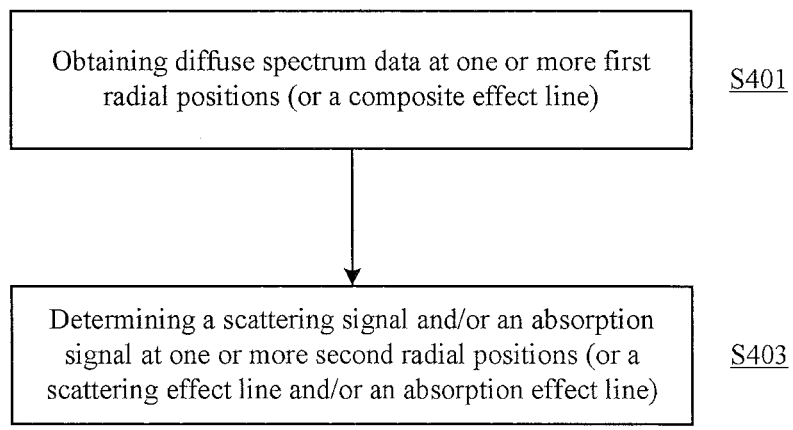
FIG. 4 is a flowchart showing a method of processing diffuse spectrum data according to an embodiment of the present disclosure.

Based on the above characteristics, there is provided a method processing diffuse spectrum data. As shown in FIG. 4, the method may comprise obtaining diffuse spectrum data of a medium to be detected at one or more first radial positions at operation S401. For example, diffuse spectrum data, such as relative variations in light intensity, at a range of continuous radial positions may constitute the above described "composite effect line." The medium to be detected may comprise various (scattering) media, such as milk and blood. For convenience of descriptions, the medium to be detected can be considered as a background medium plus a particular component in the background medium (that is, the background medium may comprise other components in the medium to be detected than the particular component). Such a particular component may be an object of interest, for example, lactose in milk, blood sugar in blood, or the like.

There are various ways in the art to detect the spectrum to obtain the diffuse spectrum data. For example, the medium to be detected may be illuminated by light at a wavelength from a light source, and diffuse reflection light and/or diffuse transmission light from the medium to be detected can be detected by a detector. For example, the intensity of the light can be detected (the light intensity at a plurality of wavelengths may constitute a spectrum). Alternatively, the light source and the detector may be immersed into the medium to be detected, to detect the diffuse spectrum data. This case is similar to the infinite medium scenario. The detector can be adjusted in position, to achieve detections at a plurality of radial positions. According to an embodiment, from data detected at at least two radial positions, detection data at other radial positions (or even the whole composite effect line) can be derived. This will be described in more detail in the following.

In addition, light at one or more wavelengths, such as ultraviolet light, visible light and infrared light, may be selected for detection based on characteristics of the medium to be detected and/or the particular component therein. For example, a wavelength at which the scattering and/or absorption characteristics of the particular component are susceptible and/or a wavelength at which the scattering and/or absorption characteristics of the background medium are insusceptible may be selected.

Advantageously, the relative variation in light intensity (caused by, for example, a variation in concentration of the particular component in the medium to be detected) may be detected as the diffuse spectrum data. For example, for the background medium without the particular component or for the background medium with the particular component at a certain initial concentration (the background medium plus the particular component at the initial concentration is called as a reference medium hereinafter), a spectrum may be detected at one or more radial positions as an initial spectrum, marked as J. Then, when the concentration of the particular component in the background medium is changed with respect to the initial concentration, a spectrum may be detected at one or more radial positions, marked as $I_2$. For example, in a case of blood sugar detection in the blood, a spectrum of the blood may be detected in an empty stomach status (in which status the blood sugar is steadily in a relatively low level) as an initial spectrum. Then, a spectrum of the blood may be detected after meal (in which status the blood sugar begins to change until it gradually turns to a steady level by about 2 hours after the meal), to obtain information on the variation of the blood sugar.

The relative variation in light intensity $S=\ln I_2 - \ln I_1$ or $s=(I_2-I_1)/I_1$ can be derived from the two spectra as the above described diffuse spectrum data. However, it is to be noted that the diffuse spectrum data are not limited to the relative variation in light intensity, and may comprise other types of data (for example, variation in light intensity) as described below.

In various embodiments of the present disclosure, there might be a need for the initial spectrum. In addition to the spectrum detected from the background medium without the particular component, the spectrum detected from the background medium with the particular component at any fixed initial concentration (that is, the reference medium) can be used as the initial spectrum. For example, a database of initial spectra may be established for some media (especially, background media without the particular component), for repeated usage (in pre-experiments or actual detections, for example), so as to reduce workload.

Further, in obtaining the spectrum data, from data detected at only a few radial positions, data at other positions can be derived because of the above described linearity rule. For example, diffuse spectrum data (for example, relative variations in light intensity) at at least two radial positions may be detected, and then diffuse spectrum data (for example, relative variations in light intensity) at other positions (especially, those close to the two radial positions) may be derived by, for example, linear fitting, with the radial positions as horizontal ordinates. Furthermore, an absolute variation in light intensity may be derived according to $\Delta I = S \cdot I_1$, where $I_1$ denotes the light intensity detected from the background medium without the particular component or with the particular component at a fixed initial concentration, that is, the initial spectrum. Especially, if one of the two points is the zero-crossing point of the composite effect line (also called as the "composite floating reference point," as shown by "215" in FIG. 2), the data at this point can be directly determined as being the initial light intensity, without further detections at this point, because this point is substantially insensitive to the concentration change of the component.

After the diffuse spectrum data (for example, the composite effect line or one or more points of the composite effect line) are obtained, the method may further comprise, at operation S403, determining optical information caused by substantially only a variation in scattering characteristic of the medium to be detected (for example, the scattering effect line or one or more points of the scattering effect line) and/or optical information caused by substantially only a variation in absorption characteristic of the medium to be detected (for example, the absorption effect line or one or more points of the absorption effect line) at one or more second radial positions from the obtained diffuse spectrum data. As described above, such extraction of the scattering effect and the absorption effect is feasible. The one or more second radial positions may be the same as or different from, or partially overlap with the one or more first radial positions.

For example, the extraction can be achieved based on a point insensitive to scattering and/or a point insensitive to absorption of the medium to be detected. Here, the so-called "point insensitive to scattering" may indicate a radial position where light intensity information included in the spectrum data is substantially insensitive to the variation in the scattering characteristic of the medium to be detected, and the so-called "point insensitive to absorption" may indicate a radial position where light intensity information included in the spectrum data is substantially insensitive to the variation in the absorption characteristic of the medium to be detected. Referring to FIG. 3, when the concentration of the particular component in the medium to be detected is changed, the point insensitive to scattering and the point insensitive to absorption have their respective positions substantially unchanged. Therefore, the point insensitive to scattering and/or the point insensitive to absorption of the medium to be detected can be detected from the background or reference medium.

The extraction of the scattering signal and/or the absorption signal based on the point insensitive to scattering and/or the point insensitive to absorption can be done as follows. Specifically, referring to FIG. 2, the scattering effect line can be derived by linear fitting based on spectrum data at the point 207 insensitive to absorption (that is, a point 213) and the point 203 insensitive to scattering or by directly connecting those two points 213 and 203 by a straight line. Similarly, the absorption effect line can be derived by linear fitting based on spectrum data at the point 203 insensitive to scattering (that is, a point 211) and the point 207 insensitive to absorption or by directly connecting those two points 211 and 207 by a straight line.

In a case where the spectrum data are detected at various wavelengths, the extraction operation may be performed on the spectrum data under the respective wavelengths based on the points insensitive to scattering and/or the points insensitive to absorption at the respective wavelengths.

Referring to FIG. 3, the scattering effect line and/or the absorption effect line (or their respective slopes) reflect the concentration change of the particular component in the medium to be detected, and thus can be used for concentration prediction, which will be described in more detail in the following.

It is to be noted that it is not necessary to extract both the scattering effect line and the absorption effect line. It suffices to only extract either one of them. For example, it is possible to perform concentration prediction based on only the scattering effect line or only the absorption effect line, as described below. Further, it is not necessary to obtain the entire scattering effect line or the entire absorption line, and it is also feasible to obtain one or more points of the scattering/absorption effect line.

In the above operations, the point insensitive to scattering and/or the point insensitive to absorption are used. For example, they can be determined as follows.

Figure 5:
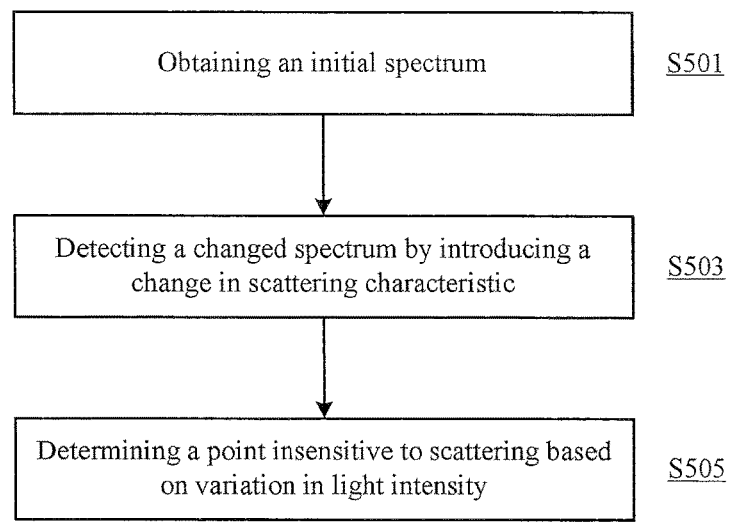
FIG. 5 is a flowchart showing a method of determining a point insensitive to scattering according to an embodiment of the present disclosure.

Referring to FIG. 5, at operation S501, a spectrum may be detected from the background or reference medium (generally, either of the background medium and the reference medium may be a scattering medium) at various radial positions under a probe light of a certain wavelength, as an initial spectrum, marked as $I_1$. Next, at operation S503, the scattering coefficient of the background or reference medium may be subjected to a slight change by, for example, adding a little amount of scattering particles, but with the absorption characteristic of the background or reference medium under this wavelength substantially unchanged (due to, for example, that the added particles exhibit substantially no absorption under this wavelength). Here, the so-called "slight" change means that such a change can cause detectable variations in the spectrum data, but in addition to this, the overall optical characteristics of the background or reference medium maintain substantially unchanged. In other words, such a slight change can be considered as a differential concept $d\mu_s'$ or $\Delta\mu_{s,j}(\lambda)$. Such a concept is commonly used in differential detections. A skilled person in the art can understand specific values and implementations of such a "slight change" based on practical applications. Here, it is to be noted that this "slight" change does not necessarily mean that it is very small in its absolute value. Likewise, a change with a relatively small absolute value is not necessarily the so-called "slight" change (for example, a change from skin of one person to skin of another person generally should not be considered as a slight change, and instead it is a change of the background medium). Then, a spectrum may be detected from the background or reference medium at various radial positions under the probe light of the same wavelength, marked as $I_2$. After that, at operation S505, a point insensitive to scattering at this wavelength can be determined from the variation in light intensity. Specifically, an absolute variation in light intensity may be calculated as $$I' = I_2 - I_1,$$

or a relative variation in light intensity may be calculated as $$S = \ln I_2 - \ln I_1 \text{ or } s = (I_2 - I_1)/I_1.$$

Because the variation in light intensity is caused by the variation in the scattering characteristic of the background or reference medium (with the absorption characteristic substantially unchanged) at operation S503, the variation in light intensity can completely reflect the variation in the scattering characteristic of the background or reference medium. A radial position corresponding to a zero-crossing point of the absolute variation I' or the relative variation S, that is, a radial position where the variation in light intensity is substantially zero, may be taken as the point insensitive to scattering, because this point indicates that the spectrum data (here, light intensity) does not vary with the scattering characteristic of the background or reference medium, i.e., insensitive to the scattering characteristic. As described above, this point can be used as the point insensitive to scattering for the medium to be used, because the concentration change of the particular component has substantially no impacts on the position of the point insensitive to scattering.

It is to be noted that the initial concentration of the particular component in the reference medium may be the same as or different from the initial concentration of the particular component in the medium to be detected when detecting the initial spectrum of the medium to be detected. Likewise, the initial concentration of the particular component in the reference medium needs not to be the same at various scenarios.

The process shown in FIG. 5 may be repeated for different wavelengths, so that points insensitive to scattering of the background medium at the respective wavelengths can be obtained.

Figure 6:
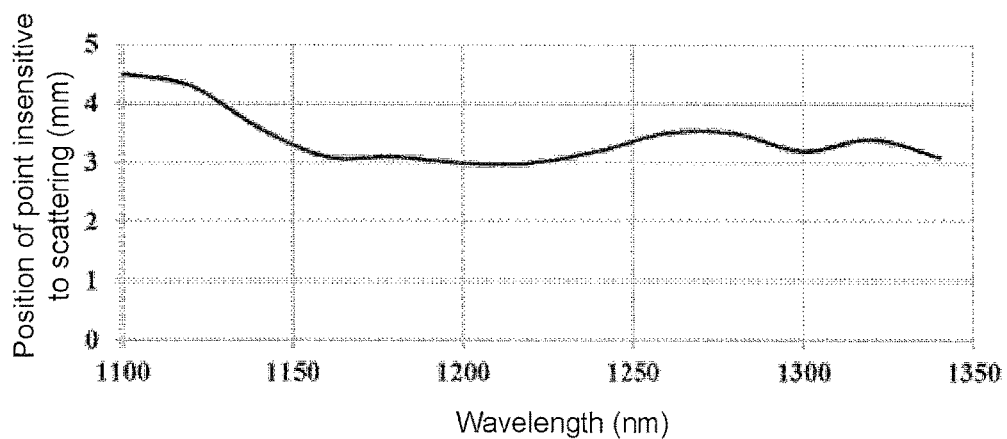
FIG. 6 is a schematic view showing positions of points insensitive to scattering at different wavelengths according to an embodiment of the present disclosure.

FIG. 6 shows experimental results for a 3% intralipid solution. This intralipid solution can mimic human skin. For example, skin of some persons has optical parameters similar to those of 3% intralipid solution, while skin of some other persons has optical parameters similar to those of 4% intralipid solution. Therefore, it is possible to perform simulation experiments with the intralipid solution to simulate in-vivo detections (for example, to simulate in-vivo detections of blood sugar by adding glucose into the intralipid solution). In such implementations, the intralipid solution can be considered as the background medium, and the glucose can be considered as the particular component. FIG. 6 shows points insensitive to scattering in a wavelength band of 1100-1340 nm.

Figure 7:
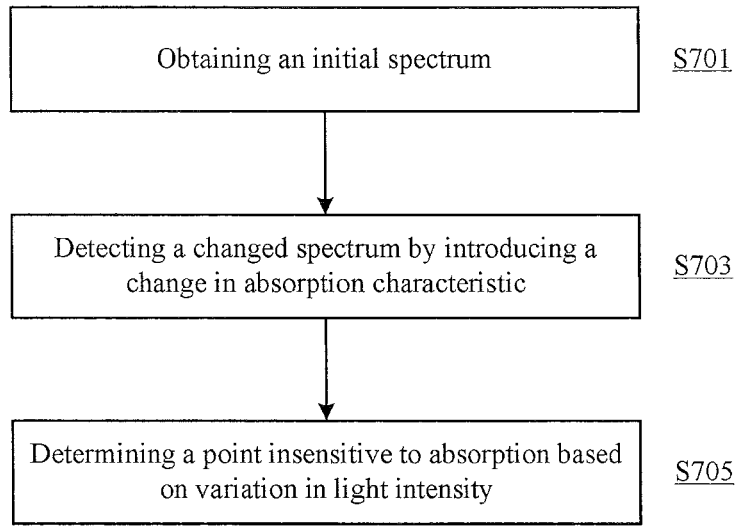
FIG. 7 is a flowchart showing a method of determining a point insensitive to absorption according to an embodiment of the present disclosure.

The point insensitive to absorption can be detected in a similar way. Referring to FIG. 7, at operation S701, a spectrum may be detected from the background or reference medium at various radial positions under a probe light of a certain wavelength, as an initial spectrum, marked as $I_1$. Next, at operation S703, the absorption coefficient of the background or reference medium may be subjected to a slight change by, for example, adding a little amount of an absorptive component, but with the scattering characteristic of the background or reference medium at this wavelength substantially unchanged (due to, for example, that the added component exhibit substantially no scattering at this wavelength). Here, regarding the so-called "slight" change, reference may be made to the above descriptions. Then, a spectrum may be detected from the background or reference medium at various radial positions under the probe light of the same wavelength, marked as $I_2$. After that, at operation S705, a point insensitive to absorption at this wavelength can be determined from the variation in light intensity. Specifically, an absolute variation in light intensity may be calculated as $I'=I_2-I_1$, or a relative variation in light intensity may be calculated as $S=\ln I_2 - \ln I_1$ or $s=(I_2-I_1)/I_1$. Because the variation in light intensity is caused by the variation in the absorption characteristic of the background or reference medium (with the scattering characteristic substantially unchanged) at operation S703, the variation in light intensity can completely reflect the variation in the absorption characteristic of the background or reference medium. A radial position corresponding to a zero-crossing point of the absolute variation $I'$ or the relative variation $S$, that is, a radial position where the variation in light intensity is substantially zero, may be taken as the point insensitive to absorption, because this point indicates that the spectrum data (here, light intensity) does not vary with the absorption characteristic of the background or reference medium, i.e., insensitive to the absorption characteristic. As described above, this point can be used as the point insensitive to absorption for the medium to be detected, because the concentration change of the particular component has substantially no impacts on the position of the point insensitive to absorption.

As described above, the initial concentration of the particular component in the reference medium when determining the point insensitive to absorption may be the same as or different from the initial concentration of the particular component in the medium to be detected when detecting the initial spectrum of the medium to be detected, and may be the same as or different from the initial concentration of the particular component in the reference medium when determining the point insensitive to scattering.

Also, the process shown in FIG. 7 may be repeated for different wavelengths, so that points insensitive to absorption of the background medium at the respective wavelengths can be obtained.

In practice, the point insensitive to absorption is generally very close to the light source. Therefore, it may be approximated by $\rho'=0$, or assume a relatively small value.

In the processes of FIGS. 5 and 7, the point insensitive to scattering and the point insensitive to absorption at the desired wavelength are determined in advance by pre-experiments. However, the present disclosure is not limited thereto. For example, the point insensitive to scattering at a target wavelength may be derived from detection data at a different wavelength. The point insensitive to absorption may be determined by the pre-experiments as described above, or may be approximated directly by a relatively small value (for example, $\rho'=0$).

Figure 8:
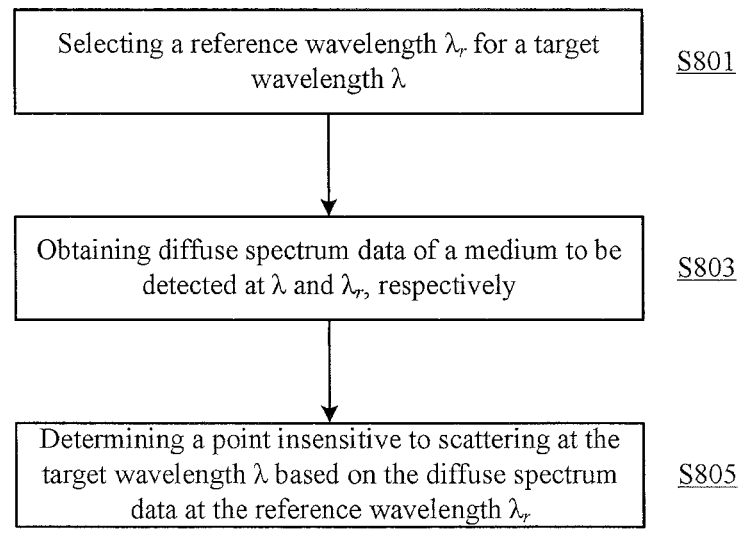
FIG. 8 is a flowchart showing a method of determining a point insensitive to scattering according to a further embodiment of the present disclosure.

Referring to FIG. 8, at operation S801, for a target wavelength $\lambda$ at which the spectrum of the medium to be detected is to be detected, a wavelength $\lambda_r$ close thereto may be selected as a reference wavelength. The reference wavelength $\lambda_r$ may be selected as a wavelength at which the particular component included in the medium to be detected has relatively weak or even no absorption. For example, in a case where the particular component comprises glucose, a wavelength of 1150 nm may be selected as the target wavelength (that is, one for detection), at which the glucose has relatively strong absorption (the absorption information can better reflect the component, as described above), and a wavelength of 1050 nm may be selected as the reference wavelength, at which the glucose has relatively weak absorption. Further, the scattering effect line at the reference wavelength $\lambda_r$, and the scattering effect line at the target wavelength $\lambda$ may be similar to each other.

Next, at operation S803, spectrum data of the medium to be detected at the respective target wavelength $\lambda$ and reference wavelength $\lambda_r$ may be obtained. The spectrum data may comprise the variation in light intensity or the relative variation in light intensity, as described above. Specifically, spectra of the medium to be detected may be detected as $I_{2,\lambda_r}$ and $I_{2,\lambda}$, and may be processed with respect to spectra $I_{1,\lambda_r}$ and $I_{1,\lambda}$ detected at an initial state (for example, a state where the background medium does not include the particular component or includes the particular component at a fixed concentration), to obtain relative variations in light intensity $S_{\lambda_r}$ and $S_\lambda$, which may be used as the spectrum data (for example, composite effect lines) at the reference wavelength $\lambda_r$ and the target wavelength $\lambda$, respectively.

Then, at operation S805, a point insensitive to scattering at the target wavelength $\lambda$ may be determined based on the spectrum data at the reference wavelength $\lambda_r$ (for example, the above described composite effect line). For example, a point $\rho_\lambda^*$ insensitive to scattering at the reference wavelength $\lambda_r$ may be determined from the spectrum data at the reference wavelength $\lambda_r$. Because the reference wavelength $\lambda_r$ is selected as one at which the medium to be detected has relatively weak or even no absorption as described above, the obtained composite effect line ($S_{\lambda_r}$) can be directly used as a scattering effect line (this is because the composite effect line in this case reflects optical information caused by the variation of the concentration of the particular component in the medium to be detected with respect to that in the initial state, and absorption information caused by the concentration variation is very small or even zero and thus is ignorable), from which the point $\rho_{\lambda_r}^*$ insensitive to scattering can be determined (as, for example, a zero-crossing point of the variation in light intensity or relative variation in light intensity). After that, the point $\rho_\lambda^*$ insensitive to scattering at the target wavelength $\lambda$ may be determined based on $\rho_{\lambda_r}^*$. For example, $\rho_{\lambda_r}^*$ may be directly used as $\rho_\lambda^*$, or may be converted to $\rho_\lambda^*$ by some simple operation. Such "simple operation" may comprise linear or two-order fitting.

Referring to Equation (7), the position of the point $\rho_\lambda^*$ insensitive to scattering depends on the effective attenuation coefficient $\mu_{eff}$. For the same background medium (or reference medium) (the concentration change of the particular component will cause substantially no change to the position of the point insensitive to scattering as described above), inferring of the points insensitive to scattering between different wavelengths can be achieved based on $\mu_{eff}$ at the wavelengths (more specifically, the absorption coefficient Pa and the scattering coefficient $\mu_s$). Mapping between different wavelengths may be determined in advance, because this is only relevant to the background medium (or reference medium) as described above. In a wavelength band where the background medium has a relatively flat absorption characteristic (for example, 1200-1250 nm), wavelengths close to each other have similar absorption characteristics (further, the scattering characteristics may be similar, so that the points insensitive to scattering at the wavelengths may be similar), and thus $\rho_{\lambda_r}^*$ may be directly used as $\rho_\lambda^*$.

The process shown in FIG. 8 is particularly suitable to media on which pre-experiments are difficult to perform, for example, in-vivo blood sugar detections. In such a case, it is difficult to carry out the processes shown in FIGS. 5 and 7 to determine the point insensitive to scattering/absorption by separately changing the scattering/absorption coefficient of the blood.

According to a further embodiment of the present disclosure, diffuse spectrum data at the point insensitive to scattering may be obtained. This can be done by, for example, directly detecting the spectrum at the point insensitive to scattering, or by deriving the spectrum data at the point insensitive to scattering from detections at at least two other positions than the point insensitive to scattering with aid of linear fitting. Referring to FIG. 2, at the point 203 insensitive to scattering, the light intensity is substantially insensitive to the variation of the scattering characteristic, and thus the (composite) diffuse spectrum data (for example, the point 211) contains a signal caused by substantially only the variation of the absorption characteristic. That is, the diffuse spectrum data at the point insensitive to scattering can be directly determined as the optical information caused by substantially only the variation in the absorption characteristic of the medium to be detected (or, the value of the absorption effect line at the point insensitive to scattering).

Similarly, diffuse spectrum data at the point insensitive to absorption may be obtained. This can be done by, for example, directly detecting the spectrum at the point insensitive to absorption, or by deriving the spectrum data at the point insensitive to absorption from detections at at least two other positions than the point insensitive to absorption with aid of linear fitting. Referring to FIG. 2, at the point 207 insensitive to absorption, the light intensity is substantially insensitive to the variation of the absorption characteristic, and thus the (composite) diffuse spectrum data (for example, the point 213) contains a signal caused by substantially only the variation of the scattering characteristic. That is, the diffuse spectrum data at the point insensitive to absorption can be directly determined as the optical information caused by substantially only the variation in the scattering characteristic of the medium to be detected (or, the value of the scattering effect line at the point insensitive to absorption). In such embodiments, the scattering information and/or the absorption information are directly extracted when obtaining the diffuse spectrum data.

In the above embodiments, the composite effect line (or one or more points thereof) is separated based on the point insensitive to scattering and/or the point insensitive to absorption, to obtain the scattering effect line and/or the absorption effect line (or one or more points thereof). However, the present disclosure is not limited thereto. For example, such a separation may be performed without depending on the point insensitive to scattering and the point insensitive to absorption.

Figure 9:
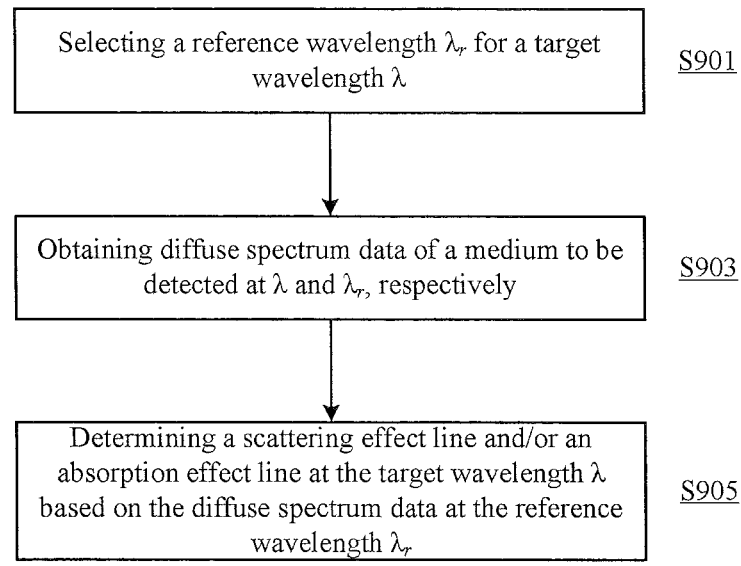
FIG. 9 is a flowchart showing a method of extracting a scatting signal and/or an absorption signal according to a further embodiment of the present disclosure.

Referring to FIG. 9, at operation S901, for a target wavelength $\lambda$ at which the spectrum of the medium to be detected is to be detected (for example, 1150 nm for glucose as described above), a wavelength $\lambda_r$ close thereto may be selected as a reference wavelength (for example, 1050 nm for glucose as described above). The reference wavelength $\lambda_r$ may be selected as a wavelength at which the particular component included in the medium to be detected has relatively weak or even no absorption. Further, the scattering effect line at the reference wavelength $\lambda_r$ may be similar to that at target wavelength $\lambda$.

Next, at operation S903, spectrum data of the medium to be detected at the respective target wavelength $\lambda$ and reference wavelength $\lambda_r$ may be obtained. The spectrum data may comprise the variation in light intensity or the relative variation in light intensity, as described above. Specifically, spectra of the medium to be detected may be detected as $I_{2,\lambda_r}$ and $I_{2,\lambda}$, and may be processed with respect to spectra and $I_{1,\lambda_r}$ and $I_{1,\lambda}$ detected at an initial state (for example, a state where the background medium does not include the particular component or includes the particular component at a fixed concentration), to obtain relative variations in light intensity $S_{\lambda_r}$ and $S_\lambda$, which may be used as the spectrum data (for example, composite effect lines) at the reference wavelength $\lambda_r$ and the target wavelength $\lambda$, respectively.

Then, at operation S905, a scattering effect line and/or an absorption effect line at the target wavelength $\lambda$ may be determined based on the spectrum data at the reference wavelength $\lambda_r$ (for example, the above described composite effect line). Because the reference wavelength $\lambda_r$ is selected as one at which the medium to be detected has relatively weak or even no absorption as described above, the obtained composite effect line ($S_{\lambda_r}$) can be directly used as a scattering effect line. The scattering effect line at the reference wavelength $\lambda_r$ may be directly used as the scattering effect line at the target wavelength $\lambda$, or may be converted into the scattering effect line at the target wavelength $\lambda$ by some simple operation. Here, due to similarity between wavelengths, such "simple operation" may comprise linear or two-order fitting. Further, the absorption effect line may be determined by subtracting the derived scattering effect line from the composite effect line ($S_\lambda$) at the target wavelength $\lambda$, to achieve the separation.

As described above, the "scattering effect line" or one or more points thereof and the "absorption effect line" or one or more points thereof, which are separated, may be used separately or in combination for concentration prediction.

Figure 10:
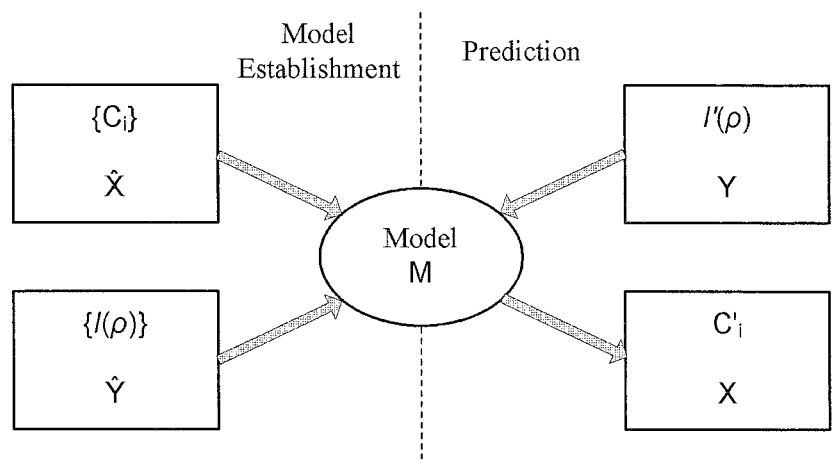
FIG. 10 is a schematic view showing a general principle of prediction model establishment and concentration prediction.

FIG. 10 shows a general principle of concentration prediction based on spectrum data. As shown in FIG. 10, a particular component may be added into a background medium or a reference medium (including the background medium and the particular component at an initial concentration) at a series of known concentrations $\{C_i\}$, from which a series of respective diffuse spectrum data $\{I(\rho)\}$ may be obtained. Based on a data set $\hat{X}$ of those known concentrations and a set $\hat{Y}$ the respective diffuse spectrum data, a prediction model M can be established. There are various ways in the art to establish the prediction model M, for example, Partial Least Square (PLS) regression. Then, for the background or reference medium (which might be different from the background or reference medium used in establishing the prediction model, as described below) with the particular component at an unknown concentration (or with an unknown concentration change) $C'_i$, corresponding diffuse spectrum data $I'(\rho)$ ("Y") may be obtained. The concentration ("X") can be predicted based on $I'(\rho)$ according to the prediction model M.

As described above, the diffuse spectrum data may comprise any suitable forms of data, such as the variation in light intensity or the relative variation in light intensity. In a case of the relative variation in light intensity, a cluster of composite effect lines (or, a cluster of corresponding scattering effect lines and/or absorption effect lines) corresponding to the respective concentrations may be obtained, as shown in FIG. 3. Further, the diffuse spectrum data may be obtained at one or more wavelengths.

In the model establishment, the spectrum of the background or reference medium may be used as an initial spectrum, and the spectra detected after the particular component is added at the known concentrations $\{C_i\}$ may be used as detected spectra. Thus, the variation in light intensity may be determined therefrom. Likewise, in the prediction, the spectrum of the background or reference medium (the initial concentration of the particular component in the reference medium may be the same as or different from the initial concentration of the particular component in the reference medium used in the model establishment) may be used as an initial spectrum, and the spectrum detected after the concentration of the particular component is changed may be used as the detected spectrum. Thus, the variation in light intensity may be determined therefrom. A result of the prediction may comprise a relative value of the concentration (i.e., a variation amount of the concentration), and may be converted to a predicted concentration by adding it to the initial value (zero in case of the background medium, or the initial concentration in case of the reference medium).

Figure 11:
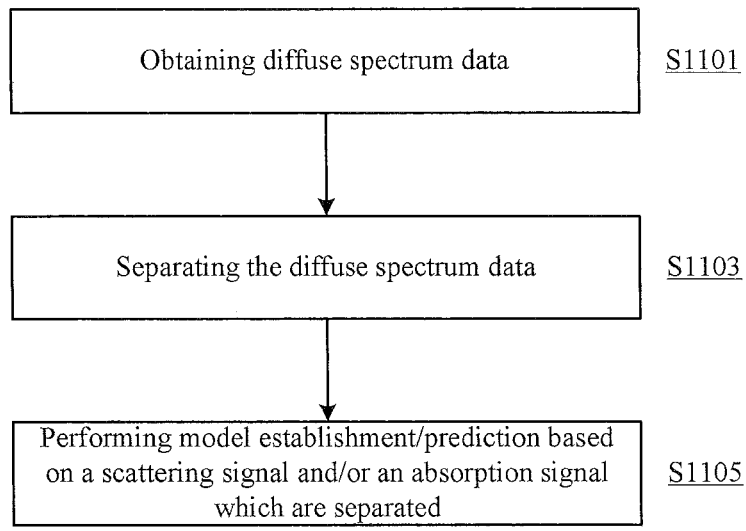
FIG. 11 is a flowchart showing a method of establishing a prediction model or predicting a concentration according to an embodiment of the present disclosure.

According to embodiments of the present disclosure, those diffuse spectrum data may be processed to extract scattering signals and/or absorption signals. For example, this separation can be done as described above. There is provided a method of establishing a prediction model and/or predicting a concentration. Referring to FIG. 11, at operation S1101, diffuse spectrum data may be obtained. For example, in the model establishment, the diffuse spectrum data may be obtained from the background or reference medium with the particular component added at the known concentrations $\{C_i\}$ (for example, the data may comprise the variation in light intensity after addition of the particular component as compared with before addition of the particular component); while in the prediction, the diffuse spectrum data may be obtained from the background or reference medium with the particular component whose concentration is changed (for example, the data may comprise the variation in light intensity after the concentration is changed as compared with before the concentration is changed). Next, at operation S1103, the diffuse spectrum data may be separated into, for example, a scattering signal (for example, a scattering line or one or more points thereof) and/or an absorption signal (for example, an absorption line or one or more points thereof). Then, at operation S1105, the model establishment or the concentration prediction may be performed based on the separated scattering signal (for example, the scattering line or one or more points thereof) and/or absorption signal (for example, the absorption line or one or more points thereof). The process of FIG. 11 proceed in almost the same way in the model establishment and in the concentration prediction, except that: in the model establishment, the concentrations of the particular component are known, and the prediction model (M) is established from the concentrations ($\hat{X}$) and the respective (processed) spectrum data ($\hat{Y}$); while in the concentration prediction, the concentration (or concentration change) of the particular component is unknown, and the concentration (or concentration change) (X) is predicted from the (processed) spectrum data (Y) according to the prediction model (M).

Specifically, the model establishment may utilize the separated scattering signal (that is, $\hat{Y}$ includes the scattering signal as spectrum data), and the prediction may also utilize the separated scattering signal (that is, Y includes the scattering signal as spectrum data). Because the scattering signal is generally stronger than the absorption signal, usage of the scattering signal in the model establishment and the prediction is advantageous in that the signal is relatively strong. However, because the scattering information may be not very distinguishable between wavelengths, it may be difficult to distinguish mixed components and thus difficult to be directly used for quantitative analysis of the mixed components.

Alternatively, the model establishment may utilize the separated absorption signal (that is, $\hat{Y}$ includes the absorption signal as spectrum data), and the prediction may also utilize the separated absorption signal (that is, Y includes the absorption signal as spectrum data). Because the absorption information is directly relevant to atom or molecule structure of substance and each component has its own specific absorption peak or band along the wavelength axis, this situation is similar to detections in pure-absorptive media, and thus is suitable for quantitative analysis of the mixed components. However, some component of interest may have relatively weak absorption, resulting in a relatively weak absorption signal, which is susceptible to noises.

Alternatively, the scattering signal and the absorption signal may be used for the model establishment and prediction, respectively, resulting in two prediction results. One from those two results may be selected based on actual environments (for example, sensitivities of scattering/absorption at different wavelengths), or the two results may be combined (by, for example, weighted averaging, wherein weights for the scattering signal and the absorption signal may be determined based on the scattering and absorption characteristics of the particular component at different wavelengths, for example, each determined as 0.5), as the prediction result.

Alternatively, both the scattering signal and the absorption signal are used for the model establishment and prediction. That is, $\hat{Y}$ may include both the scattering signal and the absorption signal as spectrum data, and Y may include both the scattering signal and the absorption signal as spectrum data.

According to a further embodiment, spectrum data at at least two radial positions may be used in the model establishment and/or prediction. For example, $\hat{Y}$ may include spectrum data (for example, variations in light intensity or relative variations in light intensity) at at least two radial positions, and Y may include spectrum data (for example, variations in light intensity or relative variations in light intensity) at at least two radial positions. The radial positions used in the model establishment and those used in the prediction are not necessarily the same. Alternatively, a slope of the scattering effect line and/or the absorption effect line may be used in the model establishment and/or prediction. For example, $\hat{Y}$ may include the slope of the scattering effect line and/or the absorption effect line as spectrum data, and Y may include the slope of the scattering effect line and/or the absorption effect line as spectrum data.

The prediction model M may be established in advance for the background/reference medium and the particular component, and saved in a database or a server, for example. The prediction model M may be retrieved from the database or the server as needed.

In the above embodiments, the detection of the spectrum data may occur at some particular radial position(s) (for example, the point insensitive to scattering and/or the point insensitive to absorption), to achieve direct extraction of the scattering signal and/or the absorption signal during the detection. In this case, the model establishment and/or prediction may be performed as follows.

Especially, for the point insensitive to scattering, the light intensity at this point is substantially insensitive to the variation of the scattering characteristic, and thus the detected data at this point comprise a signal caused by substantially only the variation of the absorption characteristic. Usage of this signal for the concentration prediction may eliminate almost all interferences from the variation of the scattering characteristic of the medium. Also, the signal is mainly consisted of two items, the initial spectrum of the medium (that is, the spectrum detected when there is no the component to be detected or the component to be detected is at a fixed initial concentration) and the variation of the absorption coefficient. Therefore, if the initial spectrum is known and is removed by mathematic methods, then the same signal—the variation of the absorption coefficient—can be derived for different scattering media. In this way, it is possible to achieve detection results consistent with those from pure-absorptive media. Based on this principle, prediction models established for scattering media with different scattering coefficients are portable. Detection of a target medium may be established from spectrum data of other scattering media or pure-absorptive media. For example, for in-vivo component detections of tissues, a model may be established by in-vitro experiments; for component detections of complex scattering media, a model may be established from scattering media in a simple system or even from pure-absorptive media. In this way, the establishment of the model is simplified in actual applications. Especially, for in-vivo detections, this method can mitigate differences in models due to differences in optical parameters of individuals.

Further, for the point insensitive to absorption, the light intensity at this point is substantially insensitive to the variation of the absorption characteristic, and thus the detected data at this point comprise a signal caused by substantially only the variation of the scattering characteristic. This signal may be used for detection of the variation of the scattering coefficient caused by the component to be detected or other factors, and also for concentration prediction based on the scattering information.

Hereinafter, examples, in which the model establishment/prediction is carried out based on the spectrum data at the point insensitive to scattering and the spectrum data at the point insensitive to absorption, respectively, will be explained.

Figure 12:
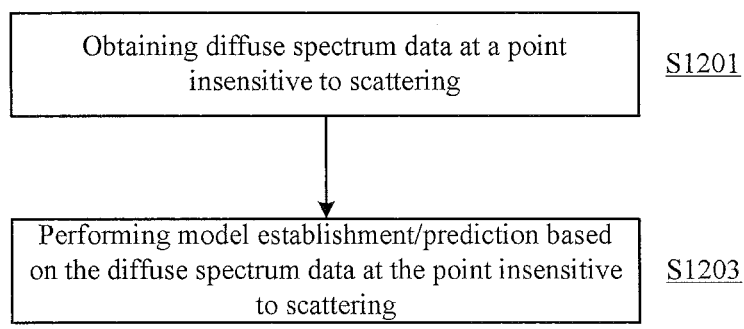
FIG. 12 is a flowchart showing a method of establishing a prediction mode or predicting a concentration based on diffuse spectrum data at a point insensitive to scattering according to an embodiment of the present disclosure.

Specifically, referring to FIG. 12, at operation S1201, spectrum data, such as a variation in light intensity or a relative variation in light intensity, at a point insensitive to scattering may be obtained. Then, at operation S1203, model establishment/prediction may be carried out based on the spectrum data at the point insensitive to scattering.

The position of the point insensitive to scattering may be determined by pre-experiments as described above (in conjunction with FIG. 5, for example), or by inter-wavelength inference (reference may be made to FIG. 8), for example.

After the point insensitive to scattering is determined, the spectrum data at this point may be obtained by detecting light intensity at (at least two) other radial positions and calculating relative variations in light intensity thereof, and then inferring the value at the point insensitive to scattering from the values at the other radial positions, instead of make a real detection at this point. Because the relative variation in light intensity exhibit linearity or approximate linearity along the radial position axis, it is possible to infer a value at one point from values at two other points. Especially, if one of the two points is the reference point for the component, then the light intensity at this point will not vary with the concentration of the component. This means that it suffices to detect only the initial spectrum at this point. In this way, data at positions where detection is relatively difficult to carry out can be derived from data at positions where detection is relatively easy to carry out. For example, some point insensitive to scattering may be far away from the light source, and light intensity at the point may be relatively weak and thus is difficult to be detected accurately. However, according to the above method, other two positions or even one position relatively close to the light source may be selected for detection, where light intensity may be relatively great and thus is relatively easy to be detected accurately. Then, light intensity at other positions can be derived therefrom.

Figure 26:
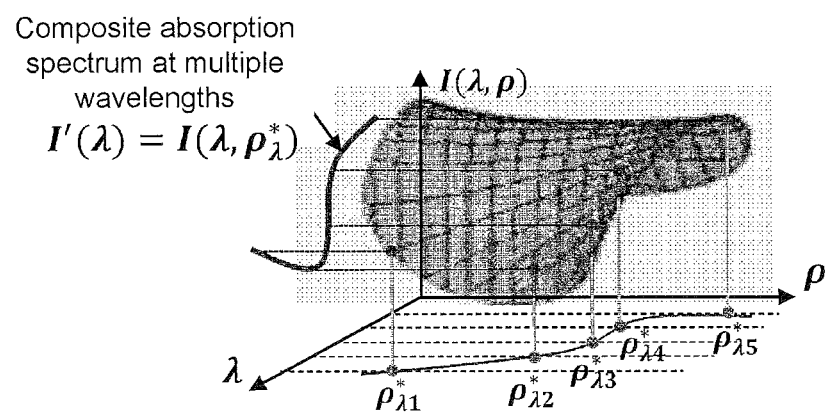
FIG. 26 is a schematic view showing obtaining spectrum data at points insensitive to scattering at different wavelengths respectively for each of the wavelengths according to an embodiment of the present disclosure.

This approach is particularly suitable for simplification of detection at points insensitive to scattering under multiple wavelengths. For example, if spectra at respective points insensitive to scattering under N wavelengths are to be detected, then detection may need to be carried out at respective one of the N points insensitive to scattering corresponding to the N wavelengths due to the dependence of the point insensitive to scattering on the wavelength (reference may be made to FIG. 6). For example, the detector may need to be moved so as to achieve detection at respective one of the N positions, as shown in FIG. 26. This is time consuming.

Figure 27:
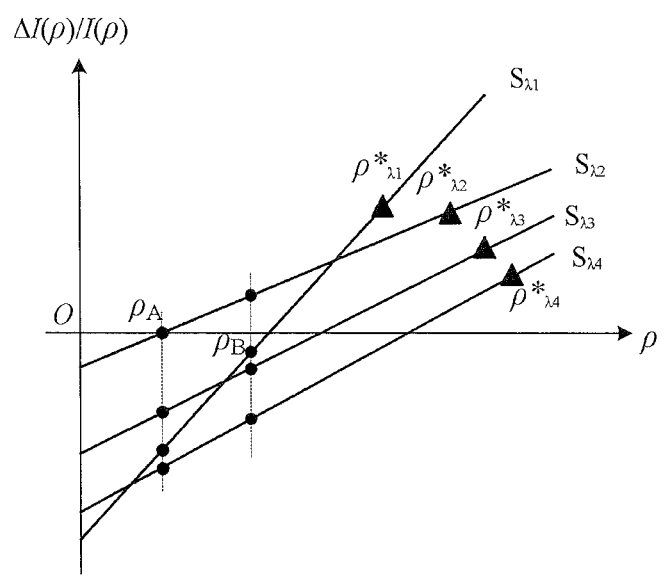
FIG. 27 is a schematic view showing obtaining spectrum data at points insensitive to scattering at different wavelengths from detection at two fixed points according to an embodiment of the present disclosure

However, according to the above approach, it is feasible to detect spectra at at least two fixed positions. For example, the light source may be fixed, and detectors may be arranged at the at least two positions to detect the spectra at the respective positions. As a result, it suffices to only change the wavelength of the light source, without need to move the detector. Then, the spectrum data at the points insensitive to scattering corresponding to the respective wavelengths may be derived from the detected spectra at the at least two positions, as described above. For example, as shown in FIG. 27, for several wavelengths $\lambda_1$, $\lambda_2$, $\lambda_3$, and $\lambda_4$, detection may be carried out at two points $\rho_A$ and $\rho_B$. If one of them is a reference point insensitive to the particular component at a certain wavelength, then there is no need to carry out detection at this point for the certain wavelength, where the initial spectrum suffices. For example, in the example shown in FIG. 27, the point $\rho_A$ is the reference point at the wavelength $\lambda_2$. Then for this wavelength $\lambda_2$, there is no need to make detection at the point $\rho_A$, where the initial spectrum suffices. As a result, it suffices to make detection at only one point (this point and also the reference point at each of the wavelengths constitute a pair of detection positions for the wavelength), provided that this point is not a reference point for any of the N wavelengths. If it is a reference point for one of the N wavelengths, then one more detection position should be selected for this wavelength. For example, in the example shown in FIG. 27, detection can be carried out at only the point $\rho_B$, which is not a reference point for any of the wavelengths $\lambda_1$, $\lambda_2$, $\lambda_3$, and $\lambda_4$. This point, together with the reference point at each of the wavelengths (where detection is not necessary, and instead may be approximated by S=0), constitutes a detection pair for the wavelength. For example, it, together with the point $\rho_A$, constitutes a detection pair for the wavelength $\lambda_2$. The S values at the respective points insensitive to scattering may be derived from the detection pair. On the other hand, if detection is carried out at only the point $\rho_A$, then one more detection position should be selected for the wavelength $\lambda_2$ to constitute a detection pair, because this point $\rho_A$ is the reference point at the wavelength $\lambda_2$.

In the model establishment and the concentration prediction based on the spectrum data at the point insensitive to scattering, the data may comprise but not limited to an absolute light intensity $I_2$ at the point insensitive to scattering (detected at the point insensitive to scattering or derived as stated above), an absolute variation in light intensity $I'=I_2-I_1$, a relative variation in light intensity $S_I=\Delta I/I=(I_2-I_1)/I_1$, an absorption coefficient $\mu_{a2}$, an absolute variation in absorption coefficient $\Delta\mu_a=\mu_{a2}-\mu_{a1}$, a relative variation in absorption coefficient $S\mu_a=\Delta\mu_a/\mu_{a1}=(\mu_{a2}-\mu_{a1})/\mu_{a1}$, an absorbance $A_2$ an absolute variation in absorbance $\Delta A=A_2-A_1$, a relative variation in absorbance $S_A=\Delta A/A=(A_2-A_1)/A_1$, or other relevant quantities constituted by any of those signals (for example, those resulted from linear transformation of any of the signals). Here, $I_1$, $\mu_{a1}$, and $A_1$ denote the initial light intensity (i.e., the light intensity detected from the background or reference medium), the initial absorption coefficient (i.e., the absorption coefficient of the background or reference medium), and the initial absorbance (i.e., the absorbance of the background or reference medium) at the point insensitive to scattering, respectively, and $I_2$, $\mu_{a2}$, and $A_2$ denote the light intensity, the absorption coefficient, and the absorbance at the point insensitive to scattering respectively after the concentration of the component to be detected is changed (that is, after the particular component is added to the background or reference medium at a known concentration in case of model establishment, or after the concentration of the particular component in the background or reference medium is changed to be unknown in case of prediction). All the above signals are caused by substantially the variation in the absorption characteristic of the particular component (because they are taken at the point insensitive to scattering), and they can be directly transformed to each other by linear transformation, as described in the following.

Specifically, the light intensity, the absorption coefficient, and the absorbance have the following theoretical relationship: $I=I_0 \cdot \exp(-\mu_a \cdot L^*)$, and $A=\mu_a \cdot L^*$, where $L^*$ denotes an average effective optical distance at the point insensitive to scattering and can be considered as a constant for one same medium, and $I_0$ denotes the light intensity emitted from the light source.

For an infinite medium, the following relationship is satisfied (at the point insensitive to scattering):

$$S_I=\Delta I/I=S_{\mu_a}=\Delta\mu_a/\mu_{a1}=S_A=\Delta A/A \quad (13)$$

Therefore, for one same medium, the relative variation in light intensity, the relative variation in absorption coefficient, and the relative variation in absorbance are equivalent to each other.

On the other hand, for a half-infinite medium, the above relationship may vary at the point insensitive to scattering. However, for the same medium to be detected, the relative variation in light intensity, the relative variation in absorption coefficient, and the relative variation in absorbance can be directly transformed to each other by linear transformation, as shown in the following equation:

$$S_I=\alpha \cdot S_{\mu_a}=\alpha \cdot S_A \quad (14)$$

where $\alpha$ is a constant for a particular medium.

In addition to the above relative variations, other signals are also transformable to each other. For example, with aid of Equation (13) or Equation (14), the light intensity metric, the absorption coefficient metric, and the absorbance metric can be associated with each other, and then the absolution variations or the absolute values of the light intensity, the absorption coefficient, and the absorbance can be derived based on the initial light intensity, the initial absorption coefficient, or the initial absorbance. For example, if the absolute light intensity at the point insensitive to scattering $I_2$ is detected or derived, then the relative variation in light intensity may be calculated by $S_I=\Delta I/I=(I_2-I_1)/I_1$ based on the initial light intensity $I_1$, and the relative variation in absorption coefficient $S\mu_a$ or the relative variation in absorbance $S_A$ may be derived based on Equation (13) or Equation (14). Further, the absorption coefficient $\mu_{a2}$ or the absorbance $A_2$ may be derived from the relative variation in absorption coefficient $S_{\mu_a}$ or the relative variation in absorbance $S_A$ in combination with the initial absorption coefficient $\mu_{a1}$ or absorbance $A_1$.

It is to be noted that the model establishment and the prediction may adopt the signals in the same form or the signals in different forms. For example, both the model establishment and the prediction may adopt the relative variation in light intensity, the relative variation in absorption coefficient, or the like. Alternatively, the model establishment may adopt the relative variation in light intensity (or other forms of signals), while the prediction may adopt the relative variation in absorption coefficient (or other forms of signals). In such a case, because all those signals are directly transformable to each other as described above, in the prediction the relative variation in absorption coefficient may be transformed into the relative variation in light intensity for input into the prediction model.

Even in a case where the model establishment and the prediction adopt the signals in different forms, the transformation (for example, transformation of the signal form adopted in the prediction into the signal form used in the model establishment as described above) may be unnecessary. In this case, great systematic errors may be caused in the prediction. However, such systematic errors can be estimated by obtaining the true value of the concentration. For example, a systematic prediction error $C_e$ and a correction coefficient k may be obtained regularly based on the true value of the concentration of the component to be detected, and then the predicted value of the concentration may be linearly corrected according to Equation (15):

$$C_{corrected} = k \cdot C_{predicted} - C_e \tag{15}$$

Here, $C_{predicted}$ denotes the predicted concentration, and $C_{corrected}$ denotes the corrected concentration.

In brief, any form of signals can be used in the model establishment and the prediction.

In a case where the model has been used for long time, if it is the initial signal obtained long time ago that is always used, then the prediction accuracy may be reduced, because there may be systematic errors caused by background variations such as tool drifting and environmental variations. The initial signal, including the initial light intensity, the initial absorption coefficient, or the initial absorbance, may be regularly updated. In updating the initial signal, the true value of the concentration of the component to be detected may be also obtained. This value can be obtained by prediction based on the model, or by detection with a method or tool at a higher accuracy. Then, the predicted concentration should be a variation with respect to the true value. Alternatively, the initial signal obtained originally may be always used, and the predicted concentration can be corrected systematically according to, for example, Equation (15).

With the above signals or other signals relevant thereto at the point insensitive to scattering, not only the detection of the particular component in the same kind of the background or reference medium can be achieved, but also the detection of the particular component in other kinds of background or reference media can be achieved by model transfer. For example, in in-vivo detections, it is difficult to obtain spectrum data at various situations by changing the component to be detected and interference components. More specifically, some component in living body has its concentration relatively steady in a short term, and it is difficult to make the concentration changed. It is relatively convenient to perform in-vitro experiments for the model establishment, and it is even more convenient to adopt pure-absorptive media in the model establishment. Therefore, if it is convenient to transform between scattering media and between scattering media and pure-absorptive media, the universality and portability of the model increase. For in-vivo spectroscopy, it promises to address difficulties such as the model is not universal and always fails due to differences in individuals.

Figure 13:
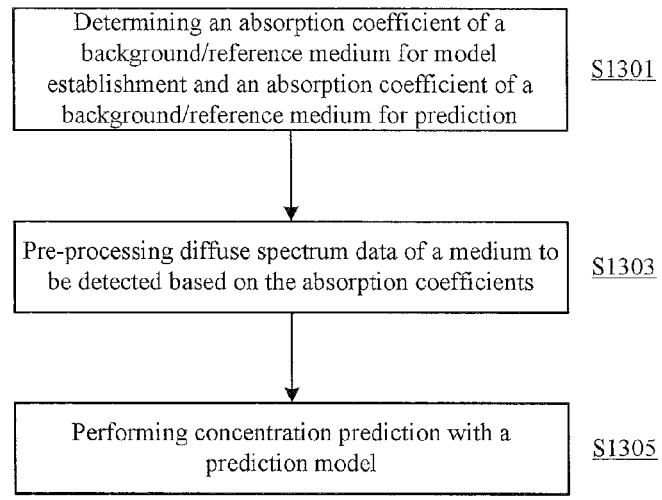
FIG. 13 is a flowchart showing a method of transferring a model between different scattering media.

Referring to FIG. 13, at operation S1301, an absorption coefficient $\mu_{a,s1}$ of a background or reference medium, which is used for establishing a (known) prediction model, and also an absorption coefficient $\mu_{a,s2}$ of a background or reference medium for prediction (which is different from that used in the model establishment; here, the so-called "different" means that the background media are not the same, for example, due to different constituent components, in addition to the possible variation in concentration of a particular component) may be detected. For example, the absorption coefficient may be detected by the integrating sphere method or other general optical parameter measuring methods. The model may be established by adding the particular component into the background or reference medium for the model establishment at a series of known concentrations and then detecting the corresponding spectra, as described above. Further, the concentration of the particular component in the background or reference medium for prediction may be changed, and then the variation in light intensity thereof may be obtained as described above.

Next, at operation S1303, diffuse spectrum data at a point insensitive to scattering of the medium for prediction may be pre-processed based on the absorption coefficients $\mu_{a,s1}$ and $\mu_{a,s2}$ (for example, a ratio there between). The diffuse spectrum data may comprise the above described signal form. For example, the pre-processing may be performed as follows based on the ratio between the absorption coefficients of the two kinds of background or reference media.

Specifically, if the model establishment and the prediction adopt the relative variation in light intensity, the relative variation in absorption coefficient, or the relative variation in absorbance, then the pre-processing may be performed as follows:

$$S_{\mu_a} = \frac{\mu_{a,s2}}{\mu_{a,s1}} \cdot S'_{\mu_a} \tag{16}$$

$$S_A = \frac{\mu_{a,s2}}{\mu_{a,s1}} \cdot S'_A$$

$$S_I = \frac{\mu_{a,s2}}{\mu_{a,s1}} \cdot S'_I$$

where $S_{\mu_a}'$ denotes the relative variation in absorption coefficient obtained from the medium for prediction, $S_{\mu_a}$ denotes a pre-processed signal obtained by pre-processing $S_{\mu_a}'$, $S_A'$ denotes the relative variation in absorbance obtained from the medium for prediction, $S_A$ denotes a pre-processed signal obtained by pre-processing $S_A'$, $S_I'$ denotes the relative variation in light intensity obtained from the medium for prediction, and $S_I$ denotes a pre-processed signal obtained by pre-processing $S_I'$. Then, the pre-processed signals may be inputted to the established model. If the background or reference medium for model establishment and the background or reference medium for prediction have their absorption coefficients similar to or substantially equal to each other, and differ from each other mainly in their scattering coefficients or reduced scattering coefficients (this may be judged based on the components of the background or reference media, for example, if the differences in their components cause substantially no change of the absorption coefficient), then the operation S1301 of measuring the absorption coefficients may be omitted, because the coefficients used in Equation (16) are almost 1 (one).

As described above, whether or not to transform the signals may be determined based on whether the same form of signals is used for the model establishment and the prediction or not. Alternatively, the transformation may be not performed, and the predicted concentration can be corrected systematically according to Equation (15).

Alternatively, the pre-processing may be not performed, and the difference in the absorption coefficients between the two media can be considered as a systematic error, and thus the predicted concentration may be corrected according to Equation (15).

Certainly, other forms of signals may be adopted. If different forms of signals are used in the model establishment and the prediction, then the signal form used in the prediction may be transformed into the signal form used in the model establishment based on above Equations (13) and (14), and the transformed signal may be inputted into the prediction model. In this case, although the signal is transformed into the same form, there may be systematic errors because the media are different and thus the initial signals thereof may be significantly different from each other. Likewise, systematic correction may be performed according to Equation (15). Alternatively, the signal transformation may be not performed, and the predicted concentration may be corrected according to Equation (15).

Alternatively, the pre-processing may be performed based on the absorption coefficient. For example, when the absolute light intensity $I_2$ is used, it may be transformed into the relative variation in light intensity $S_f = \Delta I/I = (I_2 - I_1)/I_1$, and then pre-processed according to Equation (16), resulting in the pre-processed relative variation in light intensity. The pre-processed relative variation in light intensity may be multiplied by the initial light intensity $I_1$ and then added to the initial light intensity $I_1$, resulting in the pre-processed absolute light intensity. The pre-processed absolute light intensity may be inputted into the prediction model (for example, one based on the absolute light intensity). Other forms of signals can be processed similarly.

Then, at operation S1305, a predicted concentration of the particular component in the medium for prediction may be derived according to the prediction model.

The above described pre-processing may be understood as follows.

Substitute Equation (7) to Equation (3), resulting in the relative variation in light intensity at the point insensitive to scattering (that is, the pure-absorption information):

$$S = \frac{\Delta \Phi}{\Phi} = -\frac{1}{\mu_a} \cdot \Delta \mu_a \quad (17)$$

The signal S at the point insensitive to scattering is relevant to only the absorption coefficient of the medium to be detected and the variation of the absorption coefficient, but irrelevant to the scattering coefficient or the reduced scattering coefficient. Therefore, if scattering media with different scattering coefficients have their respective absorption coefficients identical to each other, the same detection information S will be obtained.

On the other hand, for scattering media having different absorption coefficients (for example, two kinds of media whose absorption coefficients are $\mu_{a1}$ and $\mu_{a2}$, respectively), in detecting the variation in the absorption coefficient $\Delta \mu_a$ caused by the same particular component, the absorption information reflected by S only differs by a factor $1/\mu_a$. This factor may be determined by measuring $\mu_{a1}$ and $\mu_{a2}$ in advance, and then correction may be made based on a ratio therebetween.

$$S1 = -\frac{1}{\mu_{a1}} \cdot \Delta \mu_a \quad (18)$$

$$S2 = -\frac{1}{\mu_{a2}} \cdot \Delta \mu_a \quad (19)$$

$$S2 = S1 * \frac{\mu_{a1}}{\mu_{a2}} \quad (20)$$

Therefore, spectroscopy models established for different scattering media are readily portable for use.

It is to be noted that the above descriptions with respect to the model establishment/prediction based on the spectrum data at the point insensitive to scattering are also applicable to the model establishment/prediction based on the spectrum data at other point(s) of the absorption effect line. This is because that the diffuse spectrum data at any point of the absorption effect line are caused substantially by the variation in the absorption characteristic of the media (but the diffuse spectrum data at the point insensitive to scattering are relatively easy to obtain as described above).

As described above, spectroscopy models can be portable between scattering media having different scattering coefficients. In addition to this, a spectroscopy model can be obtained for a pure-absorptive background medium and used for another scattering medium, provided that the pure-absorptive background medium has its absorption coefficient similar to that of the scattering medium, or the absorption coefficients of those two may be detected in advance and then data may be transformed according to Equation (20). In establishing the model based on the pure-absorptive medium, it is equivalent to transmission detection at an optical distance of $L^* = 1/\mu_a$, which is relatively easy to implement. Further, this optical distance is an optimal one for the transmission detection, because the detection is most sensitive at this optical distance.

Figure 14:
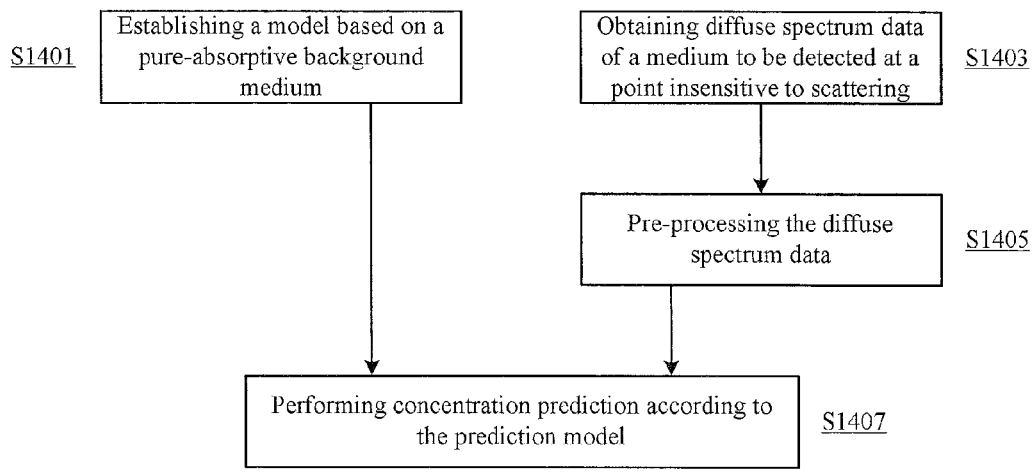
FIG. 14 is a flowchart showing a method of transferring a model between a pure-absorptive medium and a scattering medium according to an embodiment of the present disclosure.

Specifically, referring to FIG. 14, at operation S 1401, a prediction model may be established based on a pure-absorptive medium. In establishing the model, various forms of signals as described above may be used. In the following descriptions, the absorption coefficient is described by way of example. For example, the pure-absorptive background medium with a particular component at different concentrations may be detected to obtain its absorbance $A_{C_i}$, with the air or a fixed pure-absorptive medium as a background. Specifically, the absorbance $A_{C_i}$ is $A_{C_i} = \ln I - \ln I_0$, where l denotes a detected spectrum, and $I_0$ denotes a background spectrum. For a series of concentrations, a series of absorption coefficients $\mu_{a,C_i}$ may be obtained by $\mu_{a,C_i} = A/L$, where L denotes the optical distance of transmission. When the concentration is 0 (zero), $\mu_a$ is the absorption coefficient of the pure-absorptive background medium. The prediction model may be established based on the concentrations and also the relative variations of the absorption coefficients at the respective concentrations with respect to that at the initial concentration $R_i = (\mu_{a,C_i} - \mu_a)/\mu_a$. The relative variation in absorption coefficient is equivalent in substance to the relative variation in absorbance, and thus can be obtained directly from the relative variation in absorbance.

At operation S1403, diffuse spectrum data at a point insensitive to scattering of a medium to be detected may be obtained. For example, the medium to be detected may comprise a background medium and the particular component, and the diffuse spectrum data may comprise any form of signals as described above. For example, an initial spectrum may be obtained from the scattering background medium or a reference medium (the scattering background medium plus the particular component at an initial concentration), and a further spectrum may be obtained after the concentration of the particular component is changed (to an unknown one).

Next, at operation S1405, the diffuse spectrum data at the point insensitive to scattering may be pre-processed based on the absorption coefficient of the pure-absorptive background medium $\mu_a$ and an absorption coefficient of the scattering background/reference medium $\mu_a'$ (for example, a ratio there between). The pre-processing may be performed in the way as described in conjunction with FIG. 13. The absorption coefficient of the scattering background/reference medium $\mu_a'$ may be detected by the integrating sphere method or other general optical parameter measuring methods, with a background which may be the same as that used in detection of the absorbance of the pure-absorptive background medium. In a case of multiple wavelengths, the above process may be performed for respective one of the wavelengths, resulting in pre-processed signals for the respective wavelengths. Alternatively, the pre-processing may be not performed, and instead a systematic correction may be performed according to Equation (15).

Then, at operation S1407, the concentration of the particular component in the scattering background medium may be predicted according to the prediction model.

Similarly to the above embodiments where the diffuse spectrum data at the point insensitive to scattering are used, the diffuse spectrum data at the point insensitive to absorption may be also utilized.

Figure 15:
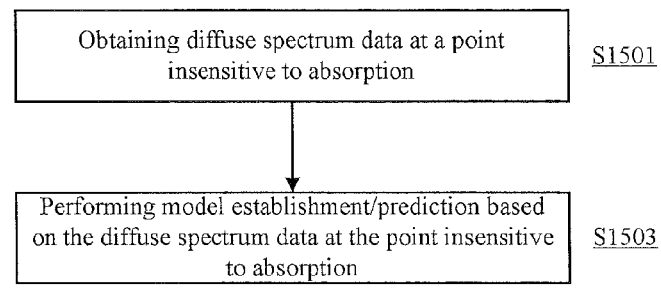
FIG. 15 is a flowchart showing a method of establishing a prediction mode or predicting a concentration based on diffuse spectrum data at a point insensitive to absorption according to an embodiment of the present disclosure.

Specifically, referring to FIG. 15, at operation S1501, spectrum data, such as a variation in light intensity or a relative variation in light intensity, at a point insensitive to absorption may be obtained. Then, at operation S1503, model establishment/prediction may be carried out based on the spectrum data at the point insensitive to scattering.

The position of the point insensitive to absorption may be determined by pre-experiments as described above (in conjunction with FIG. 7, for example), or approximated by a relatively small value (e.g., 0), for example.

After the point insensitive to absorption is determined, the spectrum data at this point may be obtained by detecting light intensity at (at least two) other radial positions and calculating relative variations in light intensity thereof, and then inferring the value at the point insensitive to absorption from the values at the other radial positions, instead of make a real detection at this point.

Similarly to the above described case where the model establishment and the prediction are based on the data at the point insensitive to scattering, in the model establishment and the concentration prediction based on the spectrum data at the point insensitive to absorption, the data may comprise but not limited to an absolute light intensity $I_2$ at the point insensitive to absorption, an absolute variation in light intensity $I'=I_2-I_1$, a relative variation in light intensity, a scattering coefficient, an absolute variation in scattering coefficient, a relative variation in scattering coefficient, or other relevant quantities. In fact, those signals are also transformable to each other, because the relative variation in light intensity is approximately equal to the relative variation in scattering coefficient or they differ from each other by only a fixed factor, as described below (that is, there is a relationship similar to that shown in Equation (13) or (14)). Therefore, the above descriptions with respect to the transformations between various signal forms, the pre-processing, and the correction (for example, those in conjunction with Equations (13)-(16)) are also applicable here.

In an example, the relative variation in light intensity at the point insensitive to absorption may be obtained as w. For example, in the model establishment, an initial spectrum may be obtained from a background or reference medium, and spectra may be obtained after a particular component is added into the background or reference medium at a series of known concentrations. Thus, the relative variation in light intensity may be derived. In the prediction, an initial spectrum may be obtained from a background or reference medium (with the particular component at a concentration the same as or different from that in the reference medium used in the model establishment), and a spectrum may be detected from the background or reference medium with the concentration of the particular component changed (to an unknown concentration). Thus, the relative variation in light intensity may be derived. If the absorption coefficient is significantly less than the scattering coefficient at the probe wavelength, then w can indicate a relative variation in scattering coefficient of the medium to be detected (referring to following Equation (21)). On the other hand, if the absorption coefficient is relatively large at the probe wavelength, then w may be transformed by being multiplied by a constant $k(\mu_a, \mu'_s)$ into $w'=w \cdot (\mu_a, \mu'_s)$. Here, k is a constant dependent on the optical parameters of the medium to be detected, $k(\mu_a, \mu'_s)=(2\mu_a+\mu'_s)/\mu'_s$, where $\mu_a$ denotes the absorption coefficient of the background or reference medium, and $\mu'_s$ denotes the reduced scattering coefficient of the background or reference medium. w' can indicate the relative variation in scattering coefficient.

If the background or reference medium for the model establishment is the same as the background or reference medium for the prediction (here, "the same" means that their constitute components may be the same, but the concentration of the particular component therein may be different), then a prediction model can be established directly based on the relative variation in scattering coefficient and the concentrations. If the background or reference medium for the model establishment is different from the background or reference medium for the prediction (here, the "different" means that the background media are different from each other, for example, due to different constitute components, in addition to possible difference in the concentration of the particular component), then model transfer may be performed as follows. For example, if the absolute variation in scattering coefficient is used in the model prediction, then in the prediction, the absolute variation in scattering coefficient may be derived from the relative variation in scattering coefficient, and then inputted into the model for concentration prediction. Alternatively, if the relative variation in scattering coefficient is used in the model prediction, then in the prediction, the relative variation in light intensity may be multiplied by a factor h, and then inputted into the prediction model. Here, h denotes a ratio of the scattering coefficients of those two media, $h=\mu_{s'medium\ to\ be\ predicted}/\mu_{s'medium\ for\ model\ establishment}$, where $\mu_{s'medium\ for\ model\ establishment}$ denotes the reduced scattering coefficient of the background or reference medium for the model establishment, and $\mu_{s'medium\ to\ be\ predicted}$ denotes the reduced scattering coefficient of the background or reference medium for the prediction.

Though the relative variation in scattering coefficient is described by way of example, the present disclosure is not limited thereto. For example, any of the above described signal forms may be used, because those signals are transformable to each other. As to the transformation and pre-processing thereof, reference may be made to the above descriptions about the various signal forms at the point insensitive to scattering, because they are similar except that the absorption coefficient is replaced with the scattering coefficient.

The above embodiments can be understood in the following way, for example.

Substituting Equation (8) into Equation (3) will result in the relative variation in light intensity at the point insensitive to absorption (i.e., the pure-absorption information):

$$S = \frac{\Delta \Phi}{\Phi} = \left(\frac{1}{2\mu_a + \mu'_s}\right) \cdot \Delta \mu'_s \quad (21)$$

The signal S at the point insensitive to absorption reflects only the scattering effect, as shown in Equation (21). Further, this point is generally close to the light source, and thus can be simplified as the position where the light source is. Especially, if for a wavelength where the absorption is relatively weak, that is, $\mu_a$ is relatively small, or if the absorption coefficient is significantly less than the scattering coefficient, that is, $\mu'_s \gg \mu_a$, the relative variation in light intensity at the point insensitive to absorption can reflect the relative variation in the scattering coefficient or the reduced scattering coefficient $\Delta\mu_s'/\mu_s'$. Such information can be well used for detecting the relative variation and the absolute variation in scattering coefficient caused by a substance when its concentration is changed.

It is to be noted that the above descriptions about the model establishment/prediction based on the diffuse spectrum data at the point insensitive to absorption are also applicable to the model establishment/prediction based on the spectrum data at other point(s) of the scattering effect line. This is because that the diffuse spectrum data at any point of the scattering effect line are caused substantially by the variation in the scattering characteristic of the media (but the diffuse spectrum data at the point insensitive to absorption are relatively easy to obtain as described above).

As described above, because the scattering signal and the absorption signal have their respective advantages and disadvantages, it is possible to achieve more accurate component detection by using the scattering signal and the absorption signal in combination for concentration prediction. Especially, some particular component (for example, glucose) exhibits relatively weak absorption, and thus if the absorption signal extracted in the above described way is directly used for predicting the glucose (according to a prediction model established in advance for the glucose), then it is necessary for detection tools to have very high precision. Further, in in-vivo detections, random errors have relatively great impact. If the scattering signal is used in addition, then it is possible to assist in or even correct the detection result from the absorption signal to some extent. This is because that the scattering signal caused by the particular component (for example, glucose) is generally significantly greater than the absorption signal caused thereby. As a result, the requirement on the precision of the detection tools is reduced. Further, the random errors in in-vivo detections can be improved.

According to an embodiment of the present disclosure, the concentration prediction may be done as follows.

Specifically, for an interference component (e.g., hemoglobin) other than the particular component (e.g., glucose) in the medium to be detected, a scattering signal thereof under a unit variation in its concentration may be obtained (in advance). For example, the concentration of this component may be changed separately (in a background medium without this interference component or with this interference component at an initial concentration; here, the so-called "background medium" is defined with respect to the interference component to be detected, that is, in this case this "interference component" is a "particular component" in the detection), diffuse spectrum data thereof may be detected, and the scattering signal may be extracted as described above. Dividing the scattering signal by the variation of the concentration results in the scattering signal per concentration variation.

For the medium to be detected (where both the particular component and the interference component may have their respective concentration changed), the data at the point insensitive to scattering (reflecting the total absorption information of the component to be detected and the interference component; and reflecting mainly the absorption of the interference component in a case where the absorption of the interference component is relatively strong, for example, significantly greater than the absorption of the particular component) may be inputted into a concentration prediction model for the interference component (for example, established in the above described way based on, for example, data at the point insensitive to scattering), to predict the concentration of the interference component. Though the data at the point insensitive to scattering are used for prediction, data at other point(s) of the absorption effect line may be used likewise, as described above.

Multiplying the predicted concentration of the interference component by the scattering signal per concentration variation will result in the scattering signal of the interference component in the medium to be detected.

From the diffuse spectrum data (e.g., the composite effect line) of the medium to be detected, the scattering signal of the interference component may be removed. For all interference components, the above process may be performed, to remove their respective effects.

The diffuse spectrum data processed as described above may be used for predicting the concentration of the component to be detected (by, for example, being inputted to a prediction model established as described above for the particular component). Here, the data at the point insensitive to absorption may be used, or data at other points than the point insensitive to scattering may be used for wavelengths where the absorption is relatively weak. In this case, it is the scattering effect of the particular component that is used for the concentration prediction, resulting in an improved accuracy of the concentration prediction because the scattering signal is relatively strong and thus a high signal to noise ratio is relatively easy to achieve.

Figure 16:
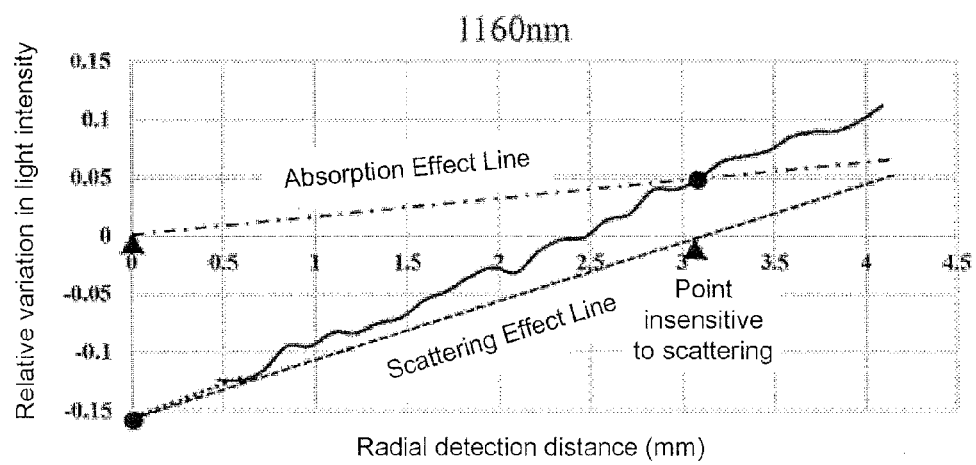
FIG. 16 is a schematic view showing separation of spectrum data for a 3% intralipid solution+10000 mg/dL glucose under a probe light at a wavelength of 1160 nm according to an embodiment of the present disclosure.

FIG. 16 shows an example composite effect line, and an absorption effect line and a scattering effect line separated therefrom. Specifically, for a 3% intralipid solution, glucose at a concentration of 10000 mg/dL is added, and then a spectrum thereof is detected. The detected spectrum is subjected to the signal separation process. FIG. 16 shows a result of the process with respect to a wavelength 1160 nm by way of example.

Figure 17:
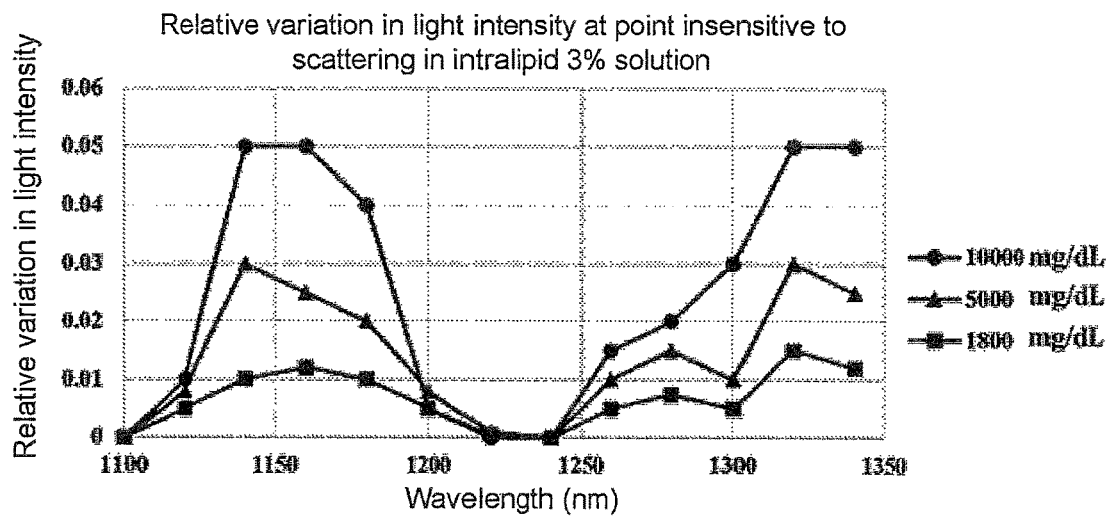
FIG. 17 is a schematic view showing pure-absorption information extracted from spectrum data for a 3% intralipid solution with glucose at different concentrations according to an embodiment of the present disclosure.

Therefore, the signal separation process for all the wavelengths will result in pure-absorption effect lines and pure-scattering effect lines. Especially, information of the pure-absorption effect can be obtained at the point insensitive to scattering, which is theoretically a relative variation in absorption coefficient. FIG. 17 shows the pure-absorption information (i.e., the relative variation in absorption coefficient) extracted at a wavelength band of 1100-1350 nm for a 3% intralipid solution with glucose added at concentrations of 1800 mg/dL, 5000 mg/dL, and 10000 mg/dL, respectively.

Figure 18:
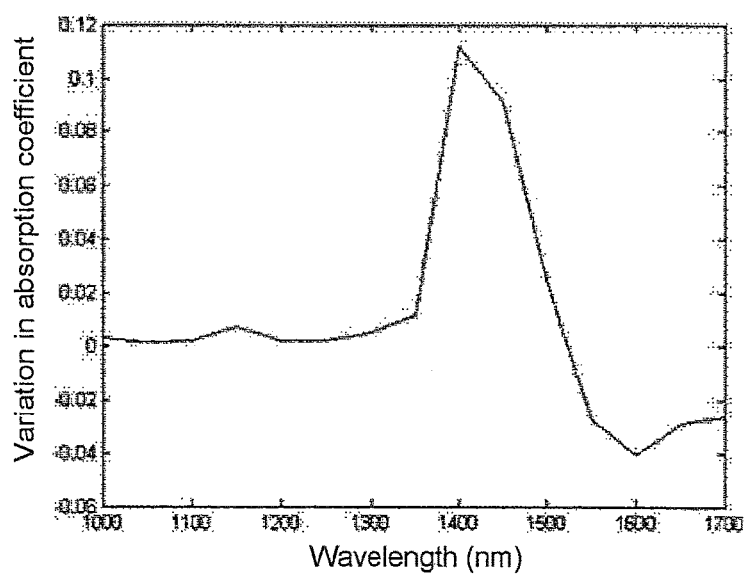
FIG. 18 is a schematic view showing an theoretical variation in absorption coefficient caused by a glucose concentration change of 50 mM according to an embodiment of the present disclosure.
Figure 19:
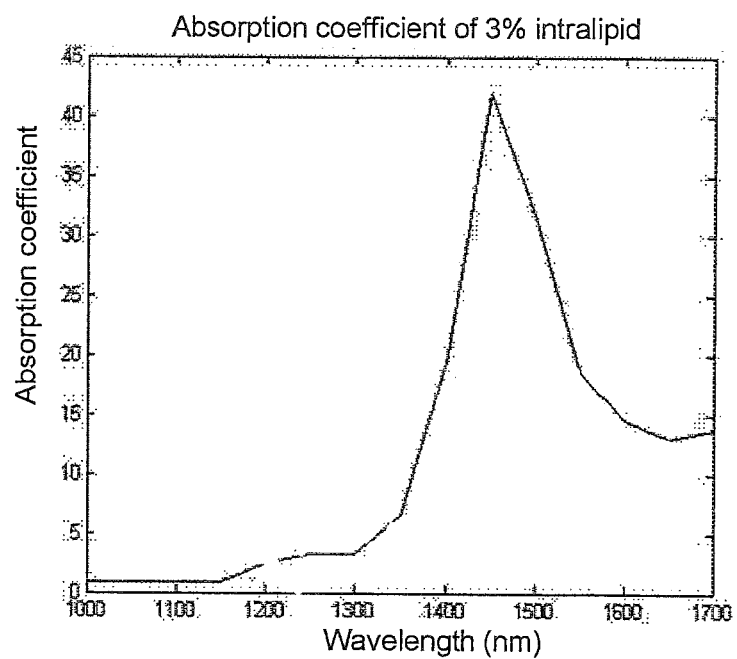
FIG. 19 is a schematic view showing absorption coefficients of a 3% intralipid solution according to an embodiment of the present disclosure.

A theoretical variation in absorption coefficient caused by a glucose concentration change of 50 mM is shown in FIG. 18, and the absorption coefficient of the 3% intralipid solution is shown in FIG. 19. A theoretical relative variation in absorption coefficient caused by the glucose is shown in FIG. 20.

Figure 20:
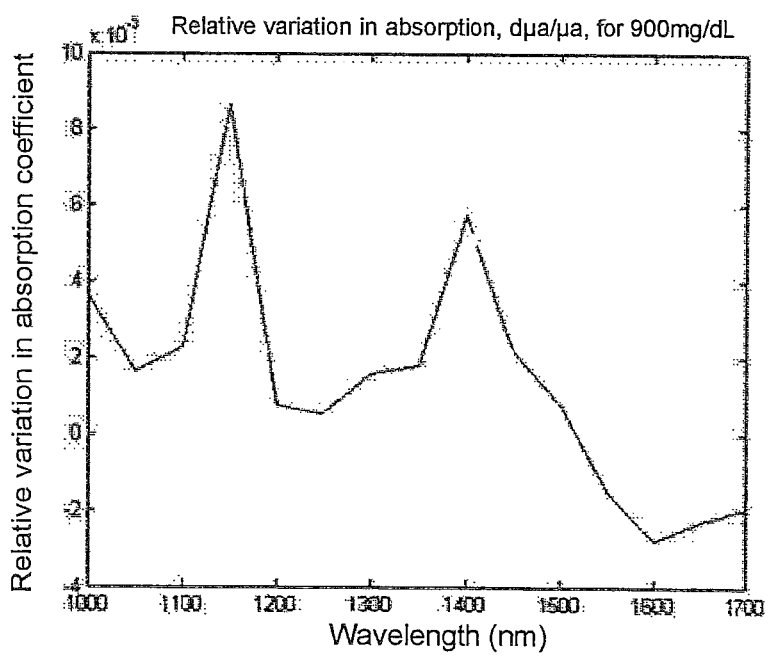
FIG. 20 is a schematic view showing a theoretical relative variation in absorption coefficient caused by glucose according to an embodiment of the present disclosure.

A comparison between FIG. 17 and FIG. 20 shows that the pure-absorption information separated from the scattering medium is similar to the theoretical absorption information of the transmission spectrum for the pure-absorptive medium at the wavelength band of 1100-1350 nm. This implies that spectroscopy models for those two media can be transferred to each other.

In another example, diffuse reflection spectra of 2%, 3%, and 4% intralipid solutions with different concentrations of glucose are simulated by Monte Carlo simulation for half-infinite medium scenario. In the simulation, optical parameters involved, including the absorption coefficient, the scattering coefficient, the anisotropy factor, and the scattering coefficient, are from Troy, the wavelength range is 1000-1700 nm, the concentration of the glucose is changed in an interval of 0-100 mM at a step of 10 mM, and the number of photons is $10^8$.

Assume that the concentration change of the glucose impacts only the scattering coefficient, but without changing the absorption coefficient, for all the wavelengths. Differential operation may be performed between light intensity results simulated for different concentrations, resulting in positions where the light intensity does not change, which is recorded as the point insensitive to scattering for the wavelength. The points insensitive to scattering for those three 2%, 3% and 4% solutions are shown in FIG. 21.

Figure 21:
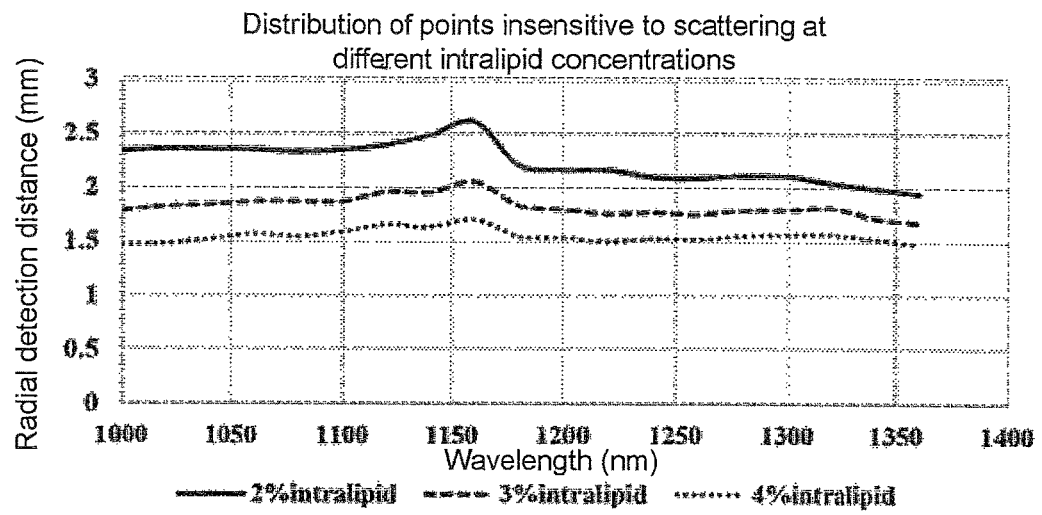
FIG. 21 is a schematic view showing positions of points insensitive to scattering at different wavelengths according to an embodiment of the present disclosure.

It is to be noted that the results for the 3% intralipid solution shown in FIGS. 6 and 21 are not completely the same. This is mainly for the following reasons. The result shown in FIG. 6 is obtained from experimental data under infinite medium scenario. The 3% intralipid solution is prepared with errors, causing the optical parameters thereof not necessarily the same as their theoretical values. On the other hand, the result of FIG. 21 is simulated under half-infinite medium scenario by inputting theoretical values of the optical parameters of the intralipid solution into a Monte Carlo simulator. The differences consist in not only the actual experiments and the computer simulation, but also in the infinite medium scenario and the half-infinite medium scenario.

Figure 22:
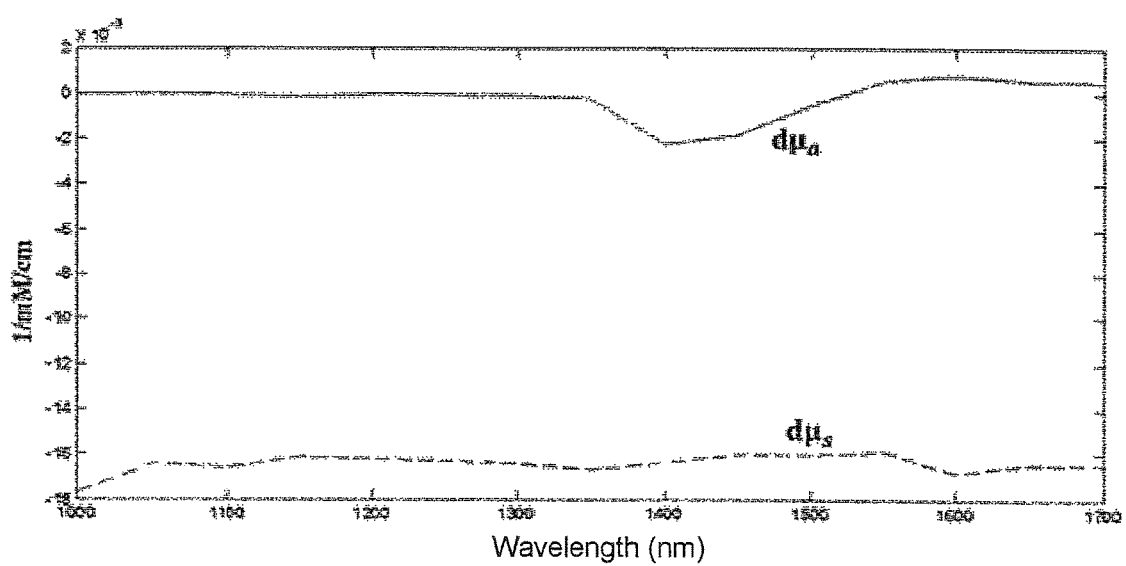
FIG. 22 is a schematic view showing variations in absorption and scattering coefficients caused by a glucose concentration change of 1 mM according to an embodiment of the present disclosure.

Then, let the glucose concentration change. Then, both the absorption coefficient and the scattering coefficient will change. The variation in light intensity is simulated. In the simulation, the variation in absorption coefficient and the variation in scattering coefficient caused by a change of the glucose concentration in a unit mM (1 mM) are shown in FIG. 22. The variation in absorption/scattering coefficient caused by other concentration change may be the variation caused by the unit concentration change multiplied by the concentration change.

The spectra at the different glucose concentrations may be subjected to differential operation with respect the initial spectrum at the glucose concentration of 0, resulting in the relative variation in light intensity caused by the glucose. Then, the signal separation process may be performed thereon, especially, at the points insensitive to scattering as shown in FIG. 21, to obtain the pure-absorption information caused by the glucose. The pure-absorption information extracted for the three media are compared, as shown in FIG. 23.

Figure 23:
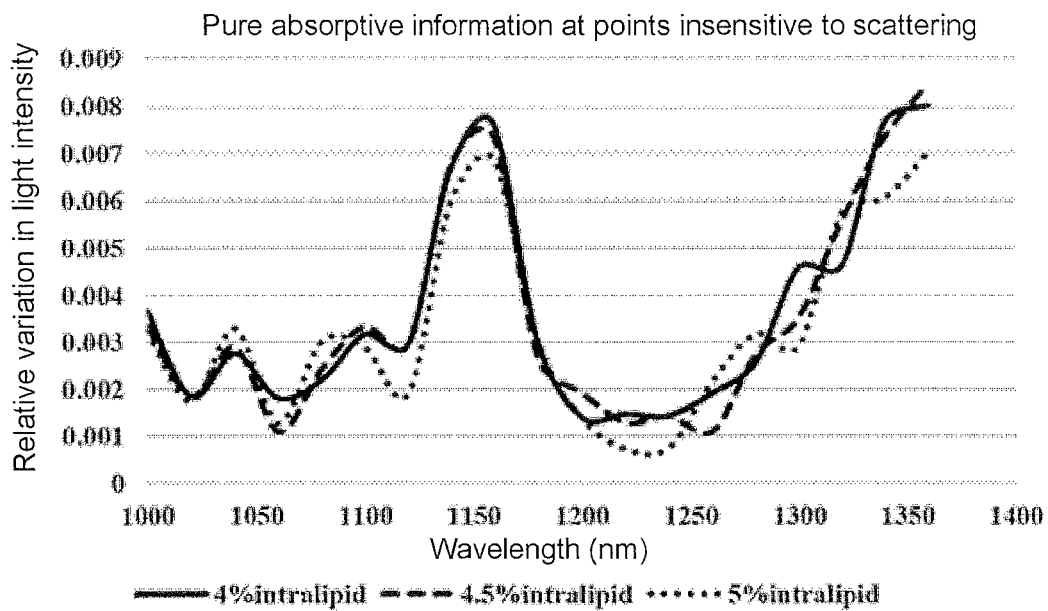
FIG. 23 is a schematic view showing absorption information caused by glucose concentration changes in different scattering media according to an embodiment of the present disclosure.

As can be seen from FIG. 23, in the half-infinite medium scenario, the different scattering media result in similar detection information at the point insensitive to scattering, and the detection information is similar in shape to the relative variation in absorption coefficient of the pure-absorptive medium. Therefore, it is possible to transfer the spectroscopy models between the scattering media and the pure-absorptive medium by simple linear transformation.

According to embodiments of the present disclosure, the scattering signal and the absorption signal may be extracted from the spectrum data, and then used for the model establishment and the prediction, respectively. Especially, the absorption signal can effectively mitigate impacts of scattering particles on the detection of the scattering medium, resulting in an improved detection precision. Further, the concentration prediction models established with respect to the absorption signals are substantially irrelevant to the scattering characteristic and the variation in the scattering characteristic of the media, and thus are portable between each other, and even between them and models established for the pure-absorptive media.

Figure 24:
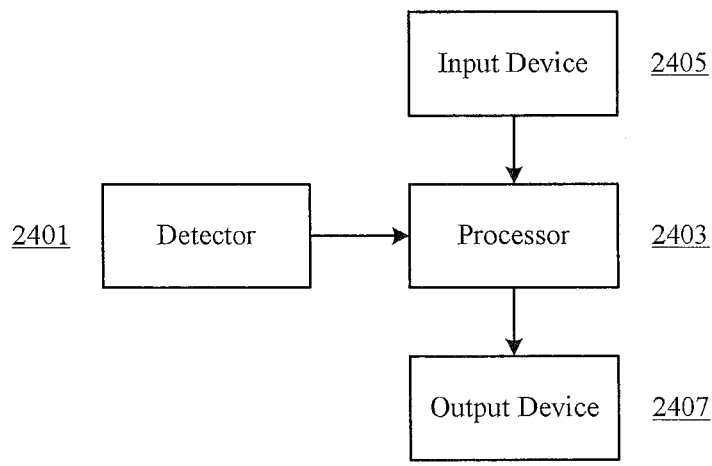
FIG. 24 is a block diagram showing a processing apparatus according to an embodiment of the present disclosure.

According to an embodiment of the present disclosure, there is also provided a processing apparatus. As shown in FIG. 24, the processing apparatus may comprise a detector 2401 (for example, a light intensity detector) configured to detect a spectrum of a medium to be detected (for example, light intensity at various radial positions). The detector 2401 may comprise one or more detectors fixed at one or more radial positions to detect spectrum data at the one or more radial positions, or alternatively a detector moveable in radial position to detect spectrum data at one or more radial positions.

The processing apparatus may further comprise a processor 2403. The processor 2403 may be configured to process the spectrum detected by the detector 2401 (for example, diffuse spectrum data at one or more first radial positions), to determine optical information caused by substantially only a variation in scattering characteristic of the medium to be detected and/or optical information caused by substantially only a variation in absorption characteristic of the medium to be detected at one or more second radial positions. The one or more second radial positions may be the same as or different from, or partially overlap with the one or more first radial positions.

The processor 2403 may comprise various forms of computing devices, such as, general computer, Application Specific Integrated Circuit (ASIC), Field Programmable Gate Array (FPGA), or the like. The processor 2403 may work in the respective flows as described above by loading programs or code segments stored in storage, to achieve scattering/absorption signal extraction, model establishment, and concentration prediction.

The processing apparatus may further comprise an input device 2405, such as, mouse, keyboard, or the like, for inputting user commands, data, or the like, and an output device 2407, such as display, for outputting process results of the processor 2403 (for example, separated scattering/absorption signals, prediction results, or the like). The input device 2405 and the output device 2407 may be implemented in combination by a touch screen.

The technology disclosed herein may also be embodied by a program comprising algorithm executable in a data processing device, or may be stored in and thus provided as a non-transitory computer readable medium.

The technology disclosed herein may also be embodied by computer readable codes on a computer readable medium. The computer readable medium may comprise a computer readable recording medium and a computer readable transmission medium. The computer readable recording medium refers to any storage device capable of storing data as a program which can be read by a computer system later. Examples of the computer readable recording medium include Read-Only Memory (ROM), Random Access Memory (RAM), Compact Disk ROM (CD-ROM), magnetic tape, floppy disk, and optical data storage. The computer readable recording medium may be distributed over a networked computer system, so that the computer readable codes are saved and executed in a distributed manner. The computer readable transmission medium can be conveyed by carriers or signals (by wired or wireless data transmission via Internet, for example). Further, functional programs, codes, and code segments to implement the technology disclosed herein can be readily interpreted by programmers in the art to which the present inventive concept belongs.

Various features of the present disclosure are described in the respective embodiments. However, this does not necessarily mean that those features cannot be used in combination to advantage.

From the foregoing, it will be appreciated that specific embodiments of the disclosure have been described herein for purposes of illustration, but that various modifications may be made without deviating from the disclosure. In addition, many of the elements of one embodiment may be combined with other embodiments in addition to or in lieu of the elements of the other embodiments. Accordingly, the technology is not limited except as by the appended claims.

We claim:

1. A method of predicting a change in concentration of a particular component in a medium to be detected with respect to a reference based on diffuse spectrum data of the medium, the method comprising:
    obtaining diffuse spectrum data of the medium at one or more first radial positions;
    determining at least one of optical information caused by substantially only a variation in scattering characteristic of the medium to be detected with respect to the reference or optical information caused by substantially only a variation in absorption characteristic of the medium to be detected with respect to the reference at one or more second radial positions from the obtained diffuse spectrum data; and
    predicting the change in concentration of the particular component based on the determined optical information.

2. The method of claim 1, wherein obtaining diffuse spectrum data comprises:
    obtaining diffuse spectrum data at at least two radial positions; and
    determining the diffuse spectrum data at the one or more first radial positions by linear fitting.

3. The method of claim 2, wherein the at least two radial positions comprises a composite reference point, which indicates a radial position where light intensity information included in the spectrum data is substantially insensitive to a variation in concentration of the particular component in the medium to be detected.

4. The method of claim 1, wherein determining optical information comprises:
    performing the determining based on at least one of a point insensitive to scattering or a point insensitive to absorption,
    wherein the point insensitive to scattering indicates a radial position where light intensity information included in the spectrum data is substantially insensitive to the variation in the scattering characteristic of the medium to be detected, and
    wherein the point insensitive to absorption indicates a radial position where light intensity information included in the spectrum data is substantially insensitive to the variation in the absorption characteristic of the medium to be detected.

5. The method of claim 4, wherein the medium to be detected comprises a background medium and the particular component included in the background medium, and wherein the method further comprises determining the point insensitive to scattering/absorption at a first wavelength by:
    preparing a scattering medium which comprises the background medium or comprises the background medium and the particular component at a certain concentration;
    obtaining light intensity variation information when a scattering/absorption coefficient of the scattering medium is changed while absorption/scattering characteristic of the scattering medium maintain substantially unchanged at the first wavelength; and
    determining the point insensitive to scattering/absorption as a radial position where the light intensity variation is substantially zero.

6. The method of claim 4, wherein the point insensitive to absorption is approximately a radial position of 0.

7. The method of claim 4, further comprising determining a plurality of points insensitive to scattering or a plurality of points insensitive to absorption at a plurality of respective wavelengths.

8. The method of claim 4, wherein the determining comprises:
    obtaining diffuse spectrum data at the at least one of the point insensitive to scattering or the point insensitive to absorption; and
    determining the optical information caused by substantially only the variation in the absorption characteristic of the medium to be detected based on the point insensitive to absorption and the diffuse spectrum data at the point insensitive to scattering, or determining the optical information caused by substantially only the variation in the scattering characteristic of the medium to be detected based on the point insensitive to scattering and the diffuse spectrum data at the point insensitive to absorption.

9. The method of claim 4, wherein
obtaining diffuse spectrum data comprises:
    selecting a second wavelength close to the first wavelength, at which the particular component included in the medium to be detected has relatively weak or substantially no absorption; and
    obtaining diffuse spectrum data at the first wavelength and the second wavelength, respectively, and
wherein the method further comprises determining the point insensitive to scattering at the first wavelength by:
    determining a point insensitive to scattering at the second wavelength as a radial position where the diffuse spectrum data at the second wavelength indicates a substantially zero variation in light intensity; and
    determining the point insensitive to scattering at the first wavelength based on the point insensitive to scattering at the second wavelength.

10. The method of claim 4, wherein
obtaining diffuse spectrum data comprises:
    obtaining diffuse spectrum data at the at least one of the point insensitive to scattering or the point insensitive to absorption, and
determining optical information comprises:
    determining the diffuse spectrum data at the point insensitive to scattering as the optical information caused by substantially only the variation in the absorption characteristic of the medium to be detected at the point insensitive to scattering, or determining the diffuse spectrum data at the point insensitive to absorption as the optical information caused by substantially only the variation in the scattering characteristic of the medium to be detected at the point insensitive to absorption.

11. The method of claim 10, wherein obtaining diffuse spectrum data comprises:
    obtaining diffuse spectrum data at the at least one of the point insensitive to scattering and/or the point insensitive to absorption for each wavelength from among a plurality of wavelengths.

12. The method of claim 11, further comprising:
obtaining diffuse spectrum data at at least one radial position fixed for each of the plurality of wavelengths, and
determining the diffuse spectrum data at the at least of the point insensitive to scattering or the point insensitive to absorption for each of the plurality of wavelengths from the obtained diffuse spectrum data.

13. The method of claim 1, wherein
obtaining diffuse spectrum data comprises:
selecting a second wavelength close to a first wavelength, at which the particular component included in the medium to be detected has relatively weak or substantially no absorption; and
obtaining diffuse spectrum data at the first wavelength and the second wavelength, respectively, and
determining optical information comprises:
determining optical information caused by substantially only the variation in the scattering characteristic of the medium to be detected at the first wavelength from the diffuse spectrum data at the second wavelength; and
determining optical information caused by substantially only the variation in the absorption characteristic of the medium to be detected at the first wavelength based on the diffuse spectrum data at the first wavelength and the determined optical information caused by substantially only the variation in the scattering characteristic of the medium to be detected at the first wavelength.

14. The method of claim 1, wherein the predicting is performed based on a prediction model, wherein the prediction model is established by:
obtaining pieces of diffuse spectrum date front a series of media, wherein each of the series of media comprises a background or reference medium with the particular component at a respective known concentration added into the background or reference medium, wherein the reference medium comprises the background medium and the particular component at an initial concentration;
determining at least of optical information caused by substantially only a variation in scattering characteristic of each of the series of media with respect to the background or reference medium or optical information caused by substantially only a variation in absorption characteristic of each of the series of media with respect to the background or reference medium at one or more second radial positions from the obtained diffuse spectrum data; and
establishing the prediction model based on the respective known concentrations and the determined optical information of the respective media.

15. The method of claim 14, wherein the optical information exhibits substantial linearity, and wherein the prediction model is established based on a slope of the optical information.

16. The method of claim claim 14, wherein the reference comprises a background or reference medium, wherein the reference medium comprises the background medium and the particular component at an initial concentration.

17. The method of claim 16, wherein the model establishing and the predicting are performed based on the optical information caused by substantially only the variation in the absorption characteristic.

18. The method of claim 17, wherein the diffuse spectrum data used in the model establishing and the predicting comprise at least one of light intensity, an absolute variation in light intensity, a relative variation in light intensity, an absorption coefficient, an absolute variation in absorption coefficient, a relative variation in absorption coefficient, or other quantities relevant thereto.

19. The method of claim 18, wherein the background or reference medium used in the model establishing is different from the background or reference medium of the medium to be predicted.

20. The method of claim 19, further comprising:
pre-processing the diffuse medium data based on a ratio of absorption coefficients between the different background or reference media, before predicting the concentration change according to the prediction model.

21. The method of claim 16, wherein the model establishing and the predicting are performed based on the optical information caused by substantially only the variation in the scattering characteristic.

22. The method of claim 21, wherein the diffuse spectrum data used in the model establishing and the predicting comprise at least one of light intensity, an absolute variation in light intensity, a relative variation in light intensity, a scattering coefficient, an absolute variation in scattering coefficient, a relative variation in scattering coefficient, or other quantities relevant thereto.

23. The method of claim 22, wherein the background or reference medium used in the model establishing is different from the background or reference medium of the medium to be predicted.

24. The method of claim 23, further comprising:
pre-processing the diffuse medium data based on a ratio of scattering coefficients between the different background or reference media, before predicting the concentration change according to the prediction model.

25. The method of claim 16, wherein predicting the concentration comprises:
obtaining a scattering signal of an interference component other than the particular component under a unit variation in concentration of the interference component;
predicting a concentration of the interference component according to a prediction model for the interference component based on the spectrum data of the medium to be detected at the point insensitive to scattering;
obtaining a further scattering signal of the interference component in the medium to be detected by multiplying the concentration of the interference component by the scattering signal under the unit variation in concentration;
removing the further scattering signal of the interference component from the spectrum data of the medium to be detected; and
predicting the concentration of the particular component based on the spectrum data with the further scattering signal of the interference component removed.

26. The method of claim 1, wherein the diffuse spectrum data comprises differential diffuse spectrum data of the medium to be detected with respect to the reference.

27. A method of predicting a concentration, comprising:
obtaining respective absorption coefficients or absorbance of a series of media, each of which comprises a pure-absorptive background medium with a particular component at a respective known concentration added into the pure-absorptive background medium;

establishing a prediction model based on the respective known concentrations and the respective absorption coefficients or absorbance;

obtaining diffuse spectrum data of a medium to be detected at a point insensitive to scattering, wherein the medium to be detected comprises a scattering background medium and the particular component at an unknown concentration due to change in concentration from an initial concentration; and predicting the concentration of the particular component according to the prediction model based on the diffuse spectrum data of the medium to be detected at the point insensitive to scattering, wherein the point insensitive to scattering indicates a radial position where light intensity information included in the spectrum data is substantially insensitive to a variation in scattering characteristic of the medium to be detected.

28. The method of claim 27, wherein the prediction model is established based on the respective known concentrations and relative variations of the respective absorption coefficients or absorbance at the respective known concentrations with respect to an absorption coefficient or absorbance at a 0 concentration of the particular component.

29. The method of claim 27, wherein the diffuse spectrum data comprise at least one of light intensity, an absolute variation in light intensity, a relative variation in light intensity, an absorption coefficient, an absolute variation in absorption coefficient, a relative variation in absorption coefficient, or other quantities relevant thereto, and is preprocessed by a ratio of absorption coefficients between the scattering background medium and the pure-absorptive background medium, for the concentration prediction according to the prediction model.

30. A processing apparatus, comprising:

a detector configured to detect a spectrum of a medium to be detected, the medium includes a particular component therein; and a processor configured to determine at least one of optical information caused by substantially only a variation in scattering characteristic of the medium to be detected with respect to a reference or optical information caused by substantially only a variation in absorption characteristic of the medium to be detected with respect to the reference at one or more radial positions from the detection of the detector, and predicting a change in concentration of the particular component with respect to the reference based on the determined optical information.

* * * * *